(12) United States Patent
Yang et al.

(10) Patent No.: US 9,714,376 B2
(45) Date of Patent: *Jul. 25, 2017

(54) SURFACTANT RESPONSIVE DISPERSION POLYMERIZED MICRO-GELS

(75) Inventors: Wei-Yeih Yang, Brecksville, OH (US); Krishnan Chari, Hudson, OH (US); Shui-Jen Raymond Hsu, Westlake, OH (US); Prachur Bhargava, Lafayette Hills, PA (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/344,816

(22) PCT Filed: Sep. 13, 2012

(86) PCT No.: PCT/US2012/055110
§ 371 (c)(1),
(2), (4) Date: Mar. 13, 2014

(87) PCT Pub. No.: WO2013/040178
PCT Pub. Date: Mar. 21, 2013

(65) Prior Publication Data
US 2014/0341957 A1 Nov. 20, 2014

Related U.S. Application Data

(60) Provisional application No. 61/578,259, filed on Dec. 21, 2011, provisional application No. 61/533,887, filed on Sep. 13, 2011, provisional application No. 61/533,884, filed on Sep. 13, 2011.

(51) Int. Cl.
| | | |
|---|---|---|
| *A61K 8/81* | (2006.01) | |
| *C09K 8/68* | (2006.01) | |
| *C08F 226/10* | (2006.01) | |
| *C08L 39/06* | (2006.01) | |
| *C09K 8/70* | (2006.01) | |
| *C09K 8/035* | (2006.01) | |
| *C09K 8/60* | (2006.01) | |
| *C08F 226/08* | (2006.01) | |
| *A61K 8/04* | (2006.01) | |
| *A61K 8/46* | (2006.01) | |
| *A61Q 5/00* | (2006.01) | |
| *A61Q 19/00* | (2006.01) | |
| *A61Q 5/02* | (2006.01) | |
| *A61Q 19/10* | (2006.01) | |

(52) U.S. Cl.
CPC .............. *C09K 8/70* (2013.01); *A61K 8/042* (2013.01); *A61K 8/463* (2013.01); *A61K 8/8182* (2013.01); *A61Q 5/00* (2013.01); *A61Q 5/02* (2013.01); *A61Q 19/00* (2013.01); *A61Q 19/10* (2013.01); *C08F 226/08* (2013.01); *C09K 8/035* (2013.01); *C09K 8/602* (2013.01); *C09K 8/604* (2013.01); *C09K 8/68* (2013.01); *A61K 2800/10* (2013.01); *C09K 2208/06* (2013.01)

(58) Field of Classification Search
None
See application file for complete search history.

(56) References Cited

U.S. PATENT DOCUMENTS

| | | | |
|---|---|---|---|
| 3,480,546 A | 11/1969 | Bashaw et al. | |
| 4,282,928 A | 8/1981 | McDonald et al. | |
| 4,384,096 A | 5/1983 | Sonnabend | |
| 5,605,685 A | 2/1997 | Tseng et al. | |
| 5,663,258 A * | 9/1997 | Zhong | C08F 226/10 526/264 |
| 5,770,760 A | 6/1998 | Robinson | |
| 6,525,129 B1 * | 2/2003 | Su | C09J 133/066 524/394 |
| 6,635,702 B1 | 10/2003 | Schmucker-Caster et al. | |
| 8,088,404 B2 * | 1/2012 | Udipi | A61L 31/10 424/426 |
| 2006/0084586 A1 | 4/2006 | Drzewinski et al. | |
| 2006/0234897 A1 | 10/2006 | Patel et al. | |
| 2009/0074695 A1 | 3/2009 | Mahe et al. | |
| 2009/0074696 A1 | 3/2009 | Biganska et al. | |
| 2010/0129307 A1 | 5/2010 | Singer et al. | |
| 2010/0184631 A1 | 7/2010 | Turner et al. | |
| 2014/0348887 A1 * | 11/2014 | Hsu et al. | 424/401 |
| 2014/0364511 A1 * | 12/2014 | Chari et al. | 514/772.6 |

FOREIGN PATENT DOCUMENTS

| | | | | |
|---|---|---|---|---|
| DE | 10243037 A1 | 3/2004 | | |
| DE | 10243038 A1 | 3/2004 | | |
| DE | 102005063376 A1 | 5/2007 | | |
| DE | WO 2009101546 A1 * | 8/2009 | | A61K 8/898 |
| EP | 0825200 A1 | 2/1998 | | |
| EP | 0870785 A1 | 10/1998 | | |
| EP | 0892039 A1 | 1/1999 | | |
| EP | 2756052 A1 | 11/2015 | | |
| GB | 1480574 A * | 7/1977 | | A61K 8/06 |
| JP | 2008-150359 A | 7/2008 | | |

(Continued)

OTHER PUBLICATIONS

Pamies, R. et al., Temperature-Induced Intermicellization and Contraction in Aqueous Mixtures of Sodium Dodecyl Sulfate and an Amphiphilic Diblock Copolymer, Journal of Colloid and Interface Science, Academic Press, New York, NY, US, vol. 326, No. 1, Oct. 1, 2008, pp. 76-88.

(Continued)

Primary Examiner — Abigail Fisher
(74) Attorney, Agent, or Firm — Thoburn T. Dunlap

(57) ABSTRACT

A stable, aqueous composition containing a crosslinked, nonionic, amphiphilic polymer capable of forming a yield stress fluid in the presence of a surfactant is disclosed. The crosslinked, nonionic amphiphilic polymer is prepared by dispersion polymerization in the presence of a stabilizing polymer. The yield stress fluid is capable of suspending insoluble materials in the form of particulates and/or droplets requiring suspension or stabilization.

40 Claims, No Drawings

(56) References Cited

FOREIGN PATENT DOCUMENTS

| WO | 91/16037 A1 | 10/1991 |
|---|---|---|
| WO | 2005/023970 A1 | 3/2005 |
| WO | 2008/060997 A1 | 5/2008 |
| WO | 2010/026097 A1 | 3/2010 |
| WO | 2011/042379 A1 | 4/2011 |
| WO | 2011/068820 A1 | 6/2011 |
| WO | WO 2011068820 A1 * | 6/2011 |
| WO | 2013/040167 A1 | 3/2013 |
| WO | 2013/040174 A1 | 3/2013 |
| WO | 2013/040178 A1 | 3/2013 |
| WO | 2013/054760 A1 | 4/2013 |

OTHER PUBLICATIONS

Dalmont, Helene et al., Study of pH-Responsive Microgels Containing Methacrylic Acid: Effects of Particle Composition and Added Calcium, Langmuir, vol. 24, No. 6, Mar. 1, 2008, pp. 2834-2840.
Kaneda, I. et al., "Rheological Properties of Water Swellable Microgel Polymerized in a Confined Space", Colloids and Surfaces, A., Physicachemical and Engineering Aspects, Elsevier, Amsterdam, NL, vol. 270-271, Dec. 1, 2005, pp. 163-170.
G.C. Maitland, "Oil and Gas Production", Current Opinion in Colloid & Interface Science, vol. 5, 2000, pp. 301-311.
Steven Abbott et al., Hansen Solubility Parameters in Practice, Complete with eBook, software and data, 5th Edition, Published by Hansen-Solubility.com, pp. 1-4 and 227-234, Copyright 2008-2015.

* cited by examiner

SURFACTANT RESPONSIVE DISPERSION POLYMERIZED MICRO-GELS

CROSS REFERENCE TO RELATED APPLICATION

This application claims priority from PCT Application Serial No. PCT/US2012/055110 filed on Sep. 13, 2012, which claims the benefit of U.S. Provisional Application No. 61/533,884 filed on Sep. 13, 2011 and on 61/533,887 filed on Sep. 13, 2011 and on 61/578,259 filed on Dec. 21, 2011.

FIELD OF THE INVENTION

The present invention relates to rheology modifiers and more specifically to a yield stress fluid comprising a surfactant responsive micro-gel. Additionally, this invention also relates to the formation of a rheologically and phase stable surfactant responsive micro-gel compositions that can be used over a broad pH range to suspend particulates and insoluble materials.

BACKGROUND OF THE INVENTION

We are surrounded in everyday life by yield stress fluids. Simply stated, yield stress fluids remain stationary until a sufficient stress is placed on the fluid at which point the fluid will flow. It can be thought of as the initial resistance to flow under stress and is also referred to as yield value. Yield stress is a measurable quantity similar to, but not dependent on viscosity. While a certain rheology modifier may thicken or enhance the viscosity of a composition in which it is included, it does not necessarily have desirable yield stress properties.

A desirable yield stress property is critical to achieving certain physical and aesthetic characteristics in a liquid medium, such as the indefinite suspension of particles, insoluble liquid droplets, or the stabilization of gas bubbles within a liquid medium. Particles dispersed in a liquid medium will remain suspended if the yield stress (yield value) of the medium is sufficient to overcome the effect of gravity or buoyancy on those particles. Insoluble liquid droplets can be prevented from rising and coalescing and gas bubbles can be suspended and uniformly distributed in a liquid medium using yield value as a formulating tool. An example of a yield stress fluid is a micro-gel rheology modifier which is used generally to adjust or modify the rheological properties of aqueous compositions. Such properties include, without limitation, viscosity, flow rate, stability to viscosity change over time, and the ability to suspend particles for indefinite periods of time. They are useful in a number of consumer and industrial applications. An important consumer application includes their use in the formulation of personal care products such as body washes, skin creams, toothpastes, shampoos, hair gels and other cosmetics. In industrial applications, they are useful as subterranean treatment fluids in the oil and gas industry as a component in drilling and fracturing fluids. Typically, they comprise chemically crosslinked polymers having a pH-responsive functionality that is either base or acid sensitive. The polymers may be mixed with other ingredients in a formulation and then neutralized by the addition of a neutralization agent such as an acid or a base. Acid sensitive thickeners are activated upon contact with an acidic agent, while base-sensitive thickeners are activated upon contact with an alkaline agent. Upon neutralization, the polymers swell significantly to form a randomly close-packed (RCP) jammed network of swollen cross-linked micro-gel particles imparting a desired rheological profile, i.e., yield stress, elastic modulus, and viscosity, as well as optical clarity to the formulation.

These types of rheology modifiers are well known in the art. For example, U.S. Pat. Nos. 2,798,053; 2,858,281; 3,032,538; and 4,758,641 describe cross-linked carboxylic acid polymers based on acrylic acid, maleic acid, itaconic acid or methacrylic acid monomers. U.S. Pat. No. 6,635,702 describes crosslinked alkali-swellable acrylate copolymers comprising one or more carboxylic acid monomers and one or more non-acid vinyl monomers. U.S. Pat. No. 7,378,479 discloses a crosslinked acid-swellable polymer containing at least one basic amino substituent that is cationic at low pH, at least one hydrophobically modified polyoxyalkylene substituent derived from an associative vinyl monomer, and at least one polyoxyalkylene substituent derived from a semi-hydrophobic vinyl surfactant monomer. A key feature of these pH-responsive micro-gels is the very large increase in diameter (or size) of individual cross-linked polymer particles upon neutralization. The high swelling efficiency allows formulators to achieve the desired yield stress and viscosity using relatively small amounts of polymer resulting in low cost-in-use. Dalmont, Pinprayoon and Saunders (*Langmuir* vol. 24, page 2834, 2008) show that individual particles in a micro-gel dispersion of a copolymer of ethyl acrylate, and methacrylic acid cross-linked with butanediol diacrylate increase in diameter by at least a factor of 3 upon pH-activation or neutralization. The level of swelling causes an increase in volume fraction of at least 27 ($3^3$). A jammed network is achieved upon neutralization (or activation) with a relatively low concentration of polymer (less than 3 wt. %).

Although pH-responsive micro-gels provide yield stress fluids with the high efficiency that is desired by the formulator, they suffer from a major disadvantage. Rheological properties are not uniform across a broad range in pH and show sharp changes as a function of pH. To overcome these difficulties various non-ionic thickeners have been proposed. U.S. Pat. No. 4,722,962 describes non-ionic associative thickeners comprising a water-soluble monoethylenically unsaturated monomer and a non-ionic urethane monomer. These polymers provide increases in viscosity or thickening of aqueous formulations that is relatively independent of pH but the polymers are not cross-linked and the purely associative interactions do not create a yield stress.

In addition to pH-responsive micro-gels, temperature-responsive micro-gels are known in the art. Senff and Richtering (*Journal of Chemical Physics*, vol. 111, page 1705, 1999) describe the change in size of non-ionic chemically cross-linked poly (N-isopropylacrylamide) (PNIPAM) micro-gel particles as a function of temperature. The particles swell by almost a factor of 2.5 in diameter (15 times in terms of volume fraction) when the temperature is reduced from 35° C. to 10° C. Although this represents a significant degree of swelling, the use of temperature to activate micro-gels is undesirable. A method of activation is needed that enables switching from a free-flowing suspension to a jammed yield stress fluid under ambient conditions.

Wu and Zhou (*Journal of Polymer Science*: Part B: Polymer Physics, vol. 34, page 1597, 1996) describe the effect of surfactant on swelling of chemically cross-linked PNIPAM homo-polymer micro-gel particles in water. The use of surfactants to activate micro-gels is attractive because many formulations contain surfactants as co-ingredients. However, the efficiency of swelling reported by Wu and Zhou is extremely low. The anionic surfactant sodium dodecyl (lauryl) sulfate increases the size of cross-linked PNIPAM particles by only a factor of 1.4 at room temperature. Furthermore, Wu and Zhou do not teach how to create a shear thinning yield stress fluid with high optical clarity.

Another inherent drawback with PNIPAM micro-gels is the low yield of polymer solids attained at the conclusion of synthesis. Thorne, Vine and Snowden (*Colloid Polymer Science*, vol. 289, page 642, 2011) report that PNIPAM prepared by surfactant free emulsion polymerization (SFEP) results in a solids concentration of 0.5% (w/v). Typical emulsion polymerized commercially available micro-gel latexes contain at least about 28% (w/v) and higher solids levels.

Hidi, Napper and Sangster (*Macromolecules*, vol. 28, page 6042, 1995) describe the effect of surfactant on swelling of poly (vinyl acetate) homopolymer micro-gels in water. For micro-gels that are not cross-linked they report an increase in diameter by a factor of 3 to 4 corresponding to a 30 to 60 fold change in volume of the original particles in the presence of sodium dodecyl (lauryl) sulfate. However, swelling is drastically reduced for cross-linked particles. In this case, they observe an increase in diameter by only a factor of 1.4. Once again, Hidi, Napper and Sangster do not teach how to create a shear thinning yield stress fluid with high optical clarity.

Apart from providing the necessary rheology profiles, the suspension of solids and/or insoluble materials in a phase stable system is as equally important to a rheology modifier. In drilling for oil and gas, subterranean treatment fluids (e.g., drilling and fracture fluids) are typically modified with gelling agents to provide desired rheological properties. Gelling agents include any substance that is capable of increasing the viscosity of a fluid, for example, by forming a micro-gel. These agents must not only possess desirable rheological properties in terms of fluid flow and pumpability, but must also have the capability to suspend solids under both dynamic and static conditions. During active drilling operations, the drilling fluid must possess sufficient structure to carry the formation cuttings to the surface and also have the necessary shear thinning properties to be pumpable. During non-drilling periods, the drilling fluid may remain stationary in the bore hole for hours or even days at a time. During this period, settling of entrained solids can be problematic if the fluid does not have enough structure to support both large and small particulate matter.

Fracturing is used to boost the production of hydrocarbons such as petroleum or natural gas from subterranean formations. In this process, a fracturing fluid containing a gelling agent is injected through a wellbore and forced against the formation strata by high pressure sufficient to cause the strata to crack and fracture thereby liberating the hydrocarbon trapped in the formation. The fracturing fluid also carries a proppant to the fracture site. Proppant particles remain in the fracture thereby "propping" the fracture open when the well is in production. The proppant material is typically selected from sand, sintered bauxite, glass balls, polystyrene beads, and the like. Whereas sufficient rheological properties are important in treatment fluids used in fracturing, satisfactory suspending ability is necessary for the transport of the proppant materials to the fracture site within the formation.

Conditions are harsh within a subterranean formation and a gelling agent must be stable to variations in temperature, brackish environments, wide ranges of pH, and changes in shear forces.

Various problems have been encountered with subterranean treatment fluids in oil field applications, including the lack of thermal stability of the gel upon exposure to varying temperatures and pH, as well as high shear conditions. This can result in changes in the rheological properties of the gel which can ultimately affect the ability of the fluid to suspend bore hole cuttings and or proppant materials. If particulate materials are prematurely lost from the treatment fluid, it can have a detrimental effect on the drilling and development of the formation. Furthermore, gel instability can result in higher loss of fluid into the formation thereby diminishing the efficiency of the operation.

Personal care compositions which can suspend particles and/or other water insoluble materials are very desirable. These materials impart or contribute to a variety of user benefits including but not limited to exfoliation, visual aesthetics, and/or the encapsulation and release of beneficial agents upon use. The suspension of particulate and insoluble materials as active and aesthetic agents in personal care compositions is becoming increasingly popular with formulators. Typically, particles are suspended in personal care compositions using structuring systems such as acrylate polymers, structuring gums (e.g., xanthan gum), starch, agar, hydroxyl alkyl cellulose, etc. However, the addition of beads or particles to personal care compositions tends to be problematic. For example, one problem is that particles or insoluble materials very frequently tend to be of a different density than the continuous phase of the composition to which they are added. This mismatch in the density can lead to separation of the particles from the continuous phase and a lack of overall product stability. In one aspect, when added particles are less dense than that of the composition continuous phase, the particles tend to rise to the top of such phase ("creaming"). In another aspect, when the added particles have a density greater than that of the continuous phase, the particles tend to gravitate to the bottom of such phase ("settling"). When large particles are desired to be suspended (e.g., polyethylene particles, guar beads, etc.), the level of polymer used is typically increased to provide increased structure for suspended beads. A consequence of thickening a liquid to provide structure for suspended beads causes a significant increase in liquid viscosity and a corresponding decrease in pourability, a property which is not always desirable. Highly viscous products are typically difficult to apply and rinse away, especially if the shear thinning profile of the viscosity building agent is deficient. High viscosities can also adversely affect packaging, dispensing, dissolution, and the foaming and sensory properties of the product. Moreover, conventionally structured liquids are often opaque or turbid thereby obscuring the suspended beads from the consumer, which adversely affects the aesthetic appeal of the product.

Many common thickeners such as xanthan gum, carboxymethylcellulose (CMC), carrageenan, and acrylic acid homopolymers and copolymers are anionic and therefore, can react with the cationic surfactants and cause precipitation of the cationic and thickener or reduce the efficacy of the cationic surfactant. Non-ionic thickeners such as hydroxyethylcellulose (HEC) and hydroxypropylmethylcellulose (HPMC) can provide viscosity in cationic systems, however, very little suspension properties are imparted to the fluid. Cationic thickeners such as Polyquaternium-10 (cationically modified HEC) and cationic guar provide thickening in cationic systems but not suspension. Some acrylic polymers are effective at thickening cationic systems but they can be limited by pH, require high concentrations, have high cost-in-use, and often have narrow limits of compatibility with the cationic materials.

Anionic surfactants are often used as detersive agents in cleansers and cleaning products because of their excellent cleaning and foaming properties. Exemplary anionic surfactants traditionally utilized in these formulations include, for example, alkyl sulfates and alkyl benzene sulfonates. While the anionic surfactants and, in particular, the anionic sulfates and sulfonates are efficient detersive agents, they are severe ocular irritants and capable of causing mild to moderate dermal irritation to some sensitized persons. Accordingly, it has become increasingly important to consumers that aqueous cleansing compositions be mild in that they do not irritate the eyes and skin when in use. Manufacturers are striving to provide mild cleansing products that also incorporate insoluble benefit and/or aesthetic agents that require stable suspension. It is known that the irritation caused by anionic sulfates and sulfonates can be reduced by utilizing the ethoxylated forms thereof. While ethoxylated surfactants may mitigate ocular and skin irritation in compositions in which they are included, a major problem in using these surfactants is that it is difficult to obtain desirable yield stress properties in an ethoxylated system.

U.S. Pat. No. 5,139,770 describes the use of crosslinked homopolymers of vinyl pyrrolidone in surfactant containing formulations such as conditioning shampoo to obtain relatively high viscosities. However, the patent does not teach how to create a yield stress fluid with high optical clarity that is also shear thinning.

U.S. Pat. No. 5,663,258 describes the preparation of crosslinked copolymers of vinyl pyrrolidone/vinyl acetate. High viscosities are obtained when the polymer is combined with water but there is no teaching about using the polymer to create a yield stress fluid that is activated by surfactant.

U.S. Pat. No. 6,645,476 discloses a water soluble polymer prepared from the free radical polymerization of a hydrophobically modified ethoxylated macromer in combination with a copolymerizable second monomer selected from unsaturated acids and their salts and/or a myriad of other monomers including N-vinyl lactams and vinyl acetate. Preferred polymers are crosslinked and are polymerized from hydrophobically modified ethoxylated macromers in combination with neutralized 2-acrylamido-2-methylpropanesulfonic acid. The viscosities of 1% aqueous solutions of the polymer preferably range from 20,000 mPa·s to 100,000 mPa·s. There is no teaching of a surfactant activated polymer devoid of hydrophobically modified ethoxylated macromer repeating units providing a yield stress fluid exhibiting good suspension properties without a substantial increase in viscosity.

There remains a challenge to not only demonstrate the ability to effectively suspend particles within stable microgel containing compositions, but also exhibit desirable mildness, desirable rheology profiles, clarity and aesthetic characteristics across a wide range of temperature and pH conditions at low polymer usage levels. Accordingly, there is a need for a yield stress fluid based on polymer micro-gel particles wherein the concentration of polymer is no more than 5 wt. % based on the weight of the composition in which it is included and having yield stress value of at least 0.1 Pa, wherein the yield stress, elastic modulus and optical clarity are substantially independent of pH. There is also a need to provide yield stress fluids formulated with mild surfactants such as, for example, surfactants containing ethylene oxide moieties.

SUMMARY OF THE INVENTION

In one aspect, embodiments of the present invention relate to crosslinked, nonionic, amphiphilic polymers that are swollen in the presence of a surfactant. In another aspect, an embodiment of the invention relates to a yield stress fluid comprising a crosslinked, nonionic, amphiphilic polymer and a surfactant.

In still another aspect, an embodiment of the invention relates to a thickened aqueous composition comprising a crosslinked, nonionic, amphiphilic polymer and at least one surfactant, wherein the concentration of the polymer is no more than 5 wt. % based on the total weight of the composition, and the at least one surfactant is no more than 30 wt. % of the composition, the yield stress of the composition is at least 0.1 Pa with a shear thinning index of less than 0.5 at shear rates between about 0.1 and about 1 reciprocal seconds, and wherein the yield stress, elastic modulus and optical clarity of the composition are substantially independent of pH in the range of about 2 to about 14.

In still another aspect, an embodiment of the invention relates to a thickened aqueous composition comprising a crosslinked, nonionic, amphiphilic polymer and at least one surfactant, wherein the concentration of the polymer is no more than 5 wt. % based on the total weight of the composition, and the at least one surfactant is no more than 30 wt. % of the composition, wherein the ratio of the standard deviation to the mean of measured values for yield stress, elastic modulus and optical clarity is less than 0.3 in one aspect, and less than 0.2 in another aspect in the pH range from about 2 to about 14.

In still another aspect, an embodiment of the invention relates to a thickened aqueous composition comprising a crosslinked, nonionic, amphiphilic polymer and at least one surfactant, wherein the concentration of the polymer is no more than 5 wt. % based on the total weight of the composition, and at least one surfactant is no more than 30 wt. % of the composition, the yield stress of the composition is at least 0.1 Pa with a shear thinning index of less than 0.5 at shear rates between about 0.1 and about 1 reciprocal seconds, and wherein the yield stress, elastic modulus and optical clarity of the composition are substantially independent of pH in the range of about 2 to about 14 and wherein the composition is able to suspend beads of a size between 0.5 and 1.5 mm wherein the difference in specific gravity of the beads relative to water is in the range of 0.2 to 0.5 for a period of at least 4 weeks at room temperature.

In still another aspect, an embodiment of the invention relates to a thickened aqueous composition comprising a crosslinked, nonionic, amphiphilic polymer and one or more surfactants, wherein the concentration of the polymer is no more than 5 wt. % based on the total weight of the composition, wherein the total concentration of surfactant is no more than 30 wt. % of the composition, the yield stress of the composition is at least 0.1 Pa with a shear thinning index of less than 0.5 at shear rates between about 0.1 and about 1 reciprocal seconds, and wherein the yield stress, elastic modulus and optical clarity of the composition are substantially independent of pH in the range of about 2 to about 14 and wherein the composition is able to suspend beads of a size between 0.5 and 1.5 mm where the difference in specific gravity of the beads relative to water is in the range of +/−0.2 to 0.5 for a period of at least 4 weeks at room temperature and wherein one of the surfactants contains ethylene oxide moieties and said surfactant is more than 75% by weight of the total surfactant.

The crosslinked, nonionic, amphiphilic polymer compositions as well as the thickened aqueous fluid comprising the nonionic, amphiphilic, polymer compositions and the at least one surfactant of the present invention may suitably comprise, consist of, or consist essentially of the components, elements, and process delineations described herein. The invention illustratively disclosed herein suitably may be practiced in the absence of any element which is not specifically disclosed herein.

Unless otherwise stated, all percentages, parts, and ratios expressed herein are based upon the total weight of the components contained in the compositions of the present invention.

By "nonionic" is meant that a monomer, monomer composition or a polymer prepared from a monomer composition is devoid of ionic or ionizable moieties ("nonionizable").

An ionizable moiety is any group that can be made ionic by neutralization with an acid or a base.

An ionic or an ionized moiety is any moiety that has been neutralized by an acid or a base.

By "substantially nonionic" is meant that the monomer, monomer composition or polymer prepared from a monomer composition contains less than 5 wt. % in one aspect, less than 3 wt. % in another aspect, less than 1 wt. % in a further aspect, less than 0.5 wt. % in a still further aspect, less than 0.1 wt. % in an additional aspect, and less than 0.05 wt. % in a further aspect, of an ionizable and/or an ionized moiety.

For the purpose of the specification, the prefix "(meth) acryl" includes "acryl" as well as "methacryl". For example, the term "(meth)acrylamide" includes both acrylamide and methacrylamide.

DESCRIPTION OF EXEMPLARY EMBODIMENTS

Exemplary embodiments in accordance with the present invention will be described. Various modifications, adaptations or variations of the exemplary embodiments described herein may become apparent to those skilled in the art as such are disclosed. It will be understood that all such modifications, adaptations or variations that rely upon the teachings of the present invention, and through which these teachings have advanced the art, are considered to be within the scope and spirit of the present invention.

While overlapping weight ranges for the various components and ingredients that can be contained in the compositions of the invention have been expressed for selected embodiments and aspects of the invention, it should be readily apparent that the specific amount of each component in the disclosed compositions will be selected from its disclosed range such that the amount of each component is adjusted such that the sum of all components in the composition will total 100 weight percent The amounts employed will vary with the purpose and character of the desired product and can be readily determined by one skilled in the art.

It has been discovered that unexpectedly highly efficient yield stress fluids with excellent shear thinning and optical clarity over a broad pH range are obtained if certain chemically crosslinked, nonionic, amphiphilic polymers are mixed with surfactants in water.

Amphiphilic Polymer

The crosslinked, nonionic, amphiphilic polymers useful in the practice of the invention are polymerized from monomer components that contain free radical polymerizable unsaturation.

In one embodiment, the crosslinked, nonionic, amphiphilic polymers useful in the practice of the invention are polymerized from a monomer composition comprising at least one nonionic, hydrophilic unsaturated monomer, at least one unsaturated hydrophobic monomer, and at least one polyunsaturated crosslinking monomer. In one aspect, the copolymer can be polymerized from a monomer composition comprising any weight ratio of nonionic, hydrophilic unsaturated monomer to unsaturated hydrophobic monomer.

In one embodiment, the copolymers can be polymerized from a monomer composition typically having a hydrophilic monomer to hydrophobic monomer ratio of from about 5:95 wt. % to about 95:5 wt. %, from about 15:85 wt. % to about 85:15 wt. % in another aspect, and from about 30:70 wt. % to about 70:30 wt. % in a further aspect, based on the total weight of the hydrophilic and hydrophobic monomers present. The hydrophilic monomer component can be selected from a single hydrophilic monomer or a mixture of hydrophilic monomers, and the hydrophobic monomer component can be selected from a single hydrophobic monomer or a mixture of hydrophobic monomers.

Hydrophilic Monomer

Representative hydrophilic monomers include but are not limited to open chain and cyclic N-vinylamides (N-vinyl lactams containing 4 to 9 atoms in the lactam ring moiety, wherein the ring carbon atoms optionally can be substituted by one or more lower alkyl groups such as methyl, ethyl or propyl); hydroxy($C_1$-$C_5$)alkyl (meth)acrylates; amino group containing vinyl monomers selected from (meth)acrylamide, N—($C_1$-$C_5$)alkyl(meth)acrylamides, N,N-di($C_1$-$C_5$) alkyl(meth)acrylamides, N—($C_1$-$C_5$)alkylamino($C_1$-$C_5$) alkyl(meth)acrylamides and N,N-di($C_1$-$C_5$)alkylamino($C_1$-$C_5$)alkyl(meth)acrylamides, wherein the alkyl moieties on the disubstituted amino groups can be the same or different, and wherein the alkyl moieties on the monosubstituted and disubstituted amino groups can be optionally substituted with a hydroxyl group; other monomers include vinyl alcohol; vinyl imidazole; and (meth)acrylonitrile. Mixtures of the foregoing monomers also can be utilized.

Representative open chain N-vinylamides include N-vinylformamide, N-methyl-N-vinylformamide, N-(hydroxymethyl)-N-vinylformamide, N-vinylacetamide, N-vinylmethylacetamide, N-(hydroxymethyl)-N-vinylacetamide, and mixtures thereof. Additionally, monomers containing a pendant N-vinyl lactam moiety can also be employed, e.g., N-vinyl-2-ethyl-2-pyrrolidone (meth)acrylate.

Representative cyclic N-vinylamides (also known as N-vinyl lactams) include N-vinyl-2-pyrrolidinone, N-(1-methyl vinyl) pyrrolidinone, N-vinyl-2-piperidone, N-vinyl-2-caprolactam, N-vinyl-5-methylpyrrolidinone, N-vinyl-3,3-dimethylpyrrolidinone, N-vinyl-5-ethyl pyrrolidinone and N-vinyl-6-methyl piperidone, and mixtures thereof.

The hydroxy($C_1$-$C_5$)alkyl (meth)acrylates can be structurally represented by the following formula:

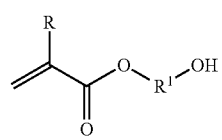

(I)

wherein R is hydrogen or methyl and $R^1$ is an divalent alkylene moiety containing 1 to 5 carbon atoms, wherein the alkylene moiety optionally can be substituted by one or more methyl groups. Representative monomers include 2-hydroxyethyl(meth)acrylate, 3-hydroxypropyl(meth)acrylate, 4-hydroxybutyl(meth)acrylate, and mixtures thereof.

The amino group containing vinyl monomers include (meth)acrylamide, diacetone acrylamide and monomers that are structurally represented by the following formulas:

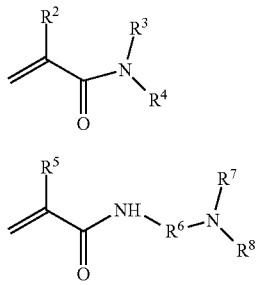

(II)

(III)

Formula (II) represents N—($C_1$-$C_5$)alkyl(meth)acrylamide or N,N-di($C_1$-$C_5$)alkyl(meth)acrylamide wherein $R^2$ is hydrogen or methyl, $R^3$ independently is selected from hydrogen, $C_1$ to $C_5$ alkyl and $C_1$ to $C_5$ hydroxyalkyl, and $R^4$ independently is selected from is $C_1$ to $C_5$ alkyl or $C_1$ to $C_5$ hydroxyalkyl.

Formula (III) represents N—($C_1$-$C_5$)alkylamino($C_1$-$C_5$) alkyl(meth)acrylamide or N,N-di($C_1$-$C_5$)alkylamino($C_1$-$C_5$) alkyl(meth)acrylamide wherein $R^5$ is hydrogen or methyl, $R^6$ is $C_1$ to $C_5$ alkylene, $R^7$ independently is selected from hydrogen or $C_1$ to $C_5$ alkyl, and $R^8$ independently is selected from $C_1$ to $C_5$ alkyl.

Representative N-alkyl(meth)acrylamides include but are not limited to N-methyl(meth)acrylamide, N-ethyl(meth)acrylamide, N-propyl(meth)acrylamide, N-isopropyl(meth)acrylamide, N-tert-butyl(meth)acrylamide, N-(2-hydroxyethyl)(meth)acrylamide, N-(3-hydroxypropyl)(meth)acrylamide, and mixtures thereof.

Representative N,N-dialkyl(meth)acrylamides include but are not limited to N,N-dimethyl(meth)acrylamide, N,N-diethyl(meth)acrylamide, N,N-(di-2-hydroxyethyl)(meth)acrylamide, N,N-(di-3-hydroxypropyl)(meth)acrylamide, N-methyl,N-ethyl(meth)acrylamide, and mixtures thereof.

Representative N,N-dialkylaminoalkyl(meth)acrylamides include but are not limited to N,N-dimethylaminoethyl (meth)acrylamide, N,N-diethylaminoethyl(meth)acrylamide, N,N-dimethylaminopropyl(meth)acrylamide, and mixtures thereof.

Hydrophobic Monomer

Hydrophobic monomers suitable for the preparation of the crosslinked, nonionic, amphiphilic polymer compositions of the invention are set forth below. In one aspect, suitable hydrophobic monomers are selected from but are not limited to one or more vinyl esters of aliphatic carboxylic acids containing 1 to 22 carbon atoms; one or more of esters of (meth)acrylic acid with alcohols containing 1 to 30 carbon atoms; one or more vinyl ethers of alcohols containing 1 to 22 carbon atoms; one or more vinyl aromatics containing 8 to 20 carbon atoms; one or more vinyl halides; one or more vinylidene halides; one or more linear or branched alpha-monoolefins containing 2 to 8 carbon atoms; an associative monomer having a hydrophobic end group containing 8 to 30 carbon atoms; and mixtures thereof.

Semi-Hydrophobic Monomer

Optionally, at least one semi-hydrophobic monomer can be used in the preparation of the amphiphilic polymers of the invention. A semi-hydrophobic monomer is similar in structure to an associative monomer, but has a substantially non-hydrophobic end group selected from hydroxyl or a moiety containing 1 to 4 carbon atoms.

In one aspect of the invention, the esters of (meth)acrylic acid with alcohols containing 1 to 30 carbon atoms can be represented by the following formula:

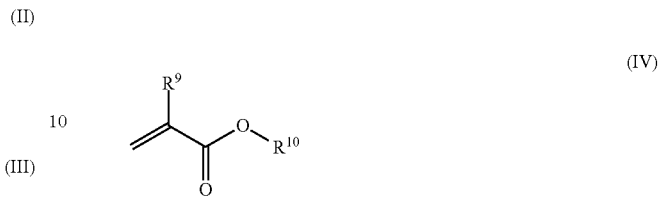

(IV)

wherein $R^9$ is hydrogen or methyl and $R^{10}$ is $C_1$ to $C_{22}$ alkyl. Representative monomers under formula (IV) include but are not limited to methyl (meth)acrylate, ethyl (meth)acrylate, butyl (meth)acrylate, sec-butyl (meth)acrylate, isobutyl (meth)acrylate, hexyl (meth)acrylate), heptyl (meth) acrylate, octyl (meth)acrylate, 2-ethylhexyl (meth)acrylate, decyl (meth)acrylate, isodecyl (meth)acrylate, lauryl (meth) acrylate, tetradecyl (meth)acrylate, hexadecyl (meth)acrylate, stearyl (meth)acrylate, behenyl (meth)acrylate, and mixtures thereof.

Vinyl esters of aliphatic carboxylic acids containing 1 to 22 carbon atoms can be represented by the following formula:

(V)

wherein $R^{11}$ is a $C_1$ to $C_{22}$ aliphatic group which can be an alkyl or alkenyl. Representative monomers under formula (V) include but are not limited to vinyl acetate, vinyl propionate, vinyl butyrate, vinyl isobutyrate, vinyl valerate, vinyl hexanoate, vinyl 2-methylhexanoate, vinyl 2-ethylhexanoate, vinyl iso-octanoate, vinyl nonanoate, vinyl neodecanoate, vinyl decanoate, vinyl versatate, vinyl laurate, vinyl palmitate, vinyl stearate, and mixtures thereof.

In one aspect, the vinyl ethers of alcohols containing 1 to 22 carbon atoms can be represented by the following formula:

(VI)

wherein $R^{13}$ is a $C_1$ to $C_{22}$ alkyl. Representative monomers of formula (VI) include methyl vinyl ether, ethyl vinyl ether, butyl vinyl ether, isobutyl vinyl ether, 2-ethylhexyl vinyl ether, decyl vinyl ether, lauryl vinyl ether, stearyl vinyl ether, behenyl vinyl ether, and mixtures thereof.

Representative vinyl aromatic monomers include but are not limited to styrene, alpha-methylstyrene, 3-methyl styrene, 4-methyl styrene, 4-propyl styrene, 4-tert-butyl styrene, 4-n-butyl styrene, 4-n-decyl styrene, vinyl naphthalene, and mixtures thereof.

Representative vinyl and vinylidene halides include but are not limited to vinyl chloride and vinylidene chloride, and mixtures thereof.

Representative alpha-olefins include but are not limited to ethylene, propylene, 1-butene, iso-butylene, 1-hexene, and mixtures thereof.

The associative monomer of the invention has an ethylenically unsaturated end group portion (i) for addition polymerization with the other monomers of the invention; a polyoxyalkylene mid-section portion (ii) for imparting selective hydrophilic and/or hydrophobic properties to the product polymer, and a hydrophobic end group portion (iii) for providing selective hydrophobic properties to the polymer.

The portion (i) supplying the ethylenically unsaturated end group can be a residue derived from an α,β-ethylenically unsaturated monocarboxylic acid. Alternatively, portion (i) of the associative monomer can be a residue derived from an allyl ether or vinyl ether; a nonionic vinyl-substituted urethane monomer, such as disclosed in U.S. Reissue Pat. No. 33,156 or U.S. Pat. No. 5,294,692; or a vinyl-substituted urea reaction product, such as disclosed in U.S. Pat. No. 5,011,978; the relevant disclosures of each are incorporated herein by reference.

The mid-section portion (ii) is a polyoxyalkylene segment of about 2 to about 150 in one aspect, from about 10 to about 120 in another aspect, and from about 15 to about 60 in a further aspect of repeating $C_2$-$C_4$ alkylene oxide units. The mid-section portion (ii) includes polyoxyethylene, polyoxypropylene, and polyoxybutylene segments, and combinations thereof comprising from about 2 to about 150 in one aspect, from about 5 to about 120 in another aspect, and from about 10 to about 60 in a further aspect of ethylene, propylene and/or butylene oxide units, arranged in random or block sequences of ethylene oxide, propylene oxide and/or butylene oxide units.

The hydrophobic end group portion (iii) of the associative monomer is a hydrocarbon moiety belonging to one of the following hydrocarbon classes: a $C_8$-$C_{30}$ linear alkyl, a $C_8$-$C_{30}$ branched alkyl, a $C_8$-$C_{30}$ carbocyclic alkyl, a $C_2$-$C_{30}$ alkyl-substituted phenyl, an araalkyl substituted phenyl, and aryl-substituted $C_2$-$C_{30}$ alkyl groups.

Non-limiting examples of suitable hydrophobic end group portions (iii) of the associative monomers are linear or branched alkyl groups having about 8 to about 30 carbon atoms, such as capryl ($C_8$), iso-octyl (branched $C_8$), decyl ($C_{10}$), lauryl ($C_{12}$), myristyl ($C_{14}$), cetyl ($C_{16}$), cetearyl ($C_{16}$-$C_{18}$), stearyl ($C_{18}$), isostearyl (branched $C_{18}$), arachidyl ($C_{20}$), behenyl ($C_{22}$), lignoceryl ($C_{24}$), cerotyl ($C_{26}$), montanyl ($C_{28}$), melissyl ($C_{30}$), and the like.

Examples of linear and branched alkyl groups having about 8 to about 30 carbon atoms that are derived from a natural source include, without being limited thereto, alkyl groups derived from hydrogenated peanut oil, soybean oil and canola oil (all predominately $C_{18}$), hydrogenated tallow oil ($C_{16}$-$C_{18}$), and the like; and hydrogenated $C_{10}$-$C_{30}$ terpenols, such as hydrogenated geraniol (branched $C_{10}$), hydrogenated farnesol (branched $C_{15}$), hydrogenated phytol (branched $C_{20}$), and the like.

Non-limiting examples of suitable $C_2$-$C_{30}$ alkyl-substituted phenyl groups include octylphenyl, nonylphenyl, decylphenyl, dodecylphenyl, hexadecylphenyl, octadecylphenyl, isooctylphenyl, sec-butylphenyl, and the like.

Exemplary aryl-substituted $C_2$-$C_{40}$ alkyl groups include, without limitation thereto, styryl (e.g., 2-phenylethyl), distyryl (e.g., 2,4-diphenylbutyl), tristyryl (e.g., 2,4,6-triphenylhexyl), 4-phenylbutyl, 2-methyl-2-phenylethyl, tristyrylphenolyl, and the like.

Suitable $C_8$-$C_{30}$ carbocylic alkyl groups include, without being limited thereto, groups derived from sterols from animal sources, such as lanosterol, 7-dehydrocholesterol, and the like; from vegetable sources, such as phytosterol, stigmasterol, campesterol, and the like; and from yeast sources, such as ergosterol, mycosterol, and the like. Other carbocyclic alkyl hydrophobic end groups useful in the present invention include, without being limited thereto, cyclooctyl, cyclododecyl, adamantyl, decahydronaphthyl, and groups derived from natural carbocyclic materials, such as pinene, hydrogenated retinol, camphor, isobornyl alcohol, and the like.

Useful associative monomers can be prepared by any method known in the art. See, for example, U.S. Pat. No. 4,421,902 to Chang et al.; U.S. Pat. No. 4,384,096 to Sonnabend; U.S. Pat. No. 4,514,552 to Shay et al.; U.S. Pat. No. 4,600,761 to Ruffner et al.; U.S. Pat. No. 4,616,074 to Ruffner; U.S. Pat. No. 5,294,692 to Barron et al.; U.S. Pat. No. 5,292,843 to Jenkins et al.; U.S. Pat. No. 5,770,760 to Robinson; and U.S. Pat. No. 5,412,142 to Wilkerson, I I I et al.; the pertinent disclosures of which are incorporated herein by reference.

In one aspect, exemplary associative monomers include those represented by formulas (VII) and (VIIA):

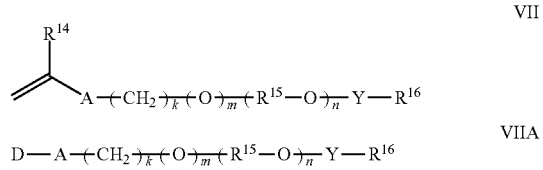

wherein $R^{14}$ is hydrogen or methyl; A is —$CH_2C(O)O$—, —$C(O)O$—, —$O$—, —$CH_2O$—, —$NHC(O)NH$—, —$C(O)NH$—, —Ar—$(CE_2)_z$-$NHC(O)O$—, —Ar—$(CE_2)_z$-$NHC(O)NH$—, or —$CH_2CH_2NHC(O)$—; Ar is a divalent arylene (e.g., phenylene); E is H or methyl; z is 0 or 1; k is an integer ranging from about 0 to about 30, and m is 0 or 1, with the proviso that when k is 0, m is 0, and when k is in the range of 1 to about 30, m is 1; D represents a vinyl or an allyl moiety; $(R^{15}$—$O)_n$ is a polyoxyalkylene moiety, which can be a homopolymer, a random copolymer, or a block copolymer of $C_2$-$C_4$ oxyalkylene units, $R^{15}$ is a divalent alkylene moiety selected from $C_2H_4$, $C_3H_6$, or $C_4H_8$, and combinations thereof; and n is an integer in the range of about 2 to about 150 in one aspect, from about 10 to about 120 in another aspect, and from about 15 to about 60 in a further aspect; Y is —$R^{15}O$—, —$R^{15}NH$—, —$C(O)$—, —$C(O)NH$—, —$R^{15}NHC(O)NH$—, or —$C(O)NHC(O)$—; $R^{16}$ is a substituted or unsubstituted alkyl selected from a $C_8$-$C_{30}$ linear alkyl, a $C_8$-$C_{30}$ branched alkyl, a $C_8$-$C_{30}$ carbocyclic alkyl, a $C_2$-$C_{30}$ alkyl-substituted phenyl, an araalkyl substituted phenyl, and an aryl-substituted $C_2$-$C_{30}$ alkyl; wherein the $R^{16}$ alkyl group, aryl group, phenyl group optionally comprises one or more substituents selected from the group consisting of a hydroxyl group, an alkoxyl group, benzyl group phenylethyl group, and a halogen group.

In one aspect, the optional hydrophobically modified associative monomer is an alkoxylated (meth)acrylate having a hydrophobic group containing 8 to 30 carbon atoms can be represented by the following formula:

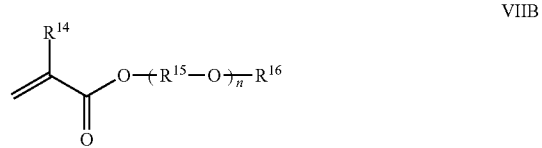

wherein $R^{14}$ is hydrogen or methyl; $R^{15}$ is a divalent alkylene moiety independently selected from $C_2H_4$, $C_3H_6$, and $C_4H_8$, and n represents an integer ranging from about 2 to about 150 in one aspect, from about 5 to about 120 in another aspect, and from about 10 to about 60 in a further aspect, ($R^{15}$—O) can be arranged in a random or a block configuration; $R^{16}$ is a substituted or unsubstituted alkyl selected from a $C_8$-$C_{30}$ linear alkyl, a $C_8$-$C_{30}$ branched alkyl, a $C_8$-$C_{30}$ carbocyclic alkyl, a $C_2$-$C_{30}$ alkyl-substituted phenyl, and an aryl-substituted $C_2$-$C_{30}$ alkyl.

Representative monomers under formula (VII) include lauryl polyethoxylated methacrylate (LEM), cetyl polyethoxylated methacrylate (OEM), cetearyl polyethoxylated methacrylate (CSEM), stearyl polyethoxylated (meth)acrylate, arachidyl polyethoxylated (meth)acrylate, behenyl polyethoxylated methacrylate (BEM), cerotyl polyethoxylated (meth)acrylate, montanyl polyethoxylated (meth)acrylate, melissyl polyethoxylated (meth)acrylate, phenyl polyethoxylated (meth)acrylate, nonylphenyl polyethoxylated (meth)acrylate, ω-tristyrylphenyl polyoxyethylene methacrylate, where the polyethoxylated portion of the monomer contains about 2 to about 150 ethylene oxide units in one aspect, from about 5 to about 120 in another aspect, and from about 10 to about 60 in a further aspect; octyloxy polyethyleneglycol (8) polypropyleneglycol (6) (meth)acrylate, phenoxy polyethylene glycol (6) polypropylene glycol (6) (meth)acrylate, and nonylphenoxy polyethylene glycol polypropylene glycol (meth)acrylate.

The polyoxyalkylene mid-section portion (ii) specifically comprises a polyoxyalkylene segment, which is substantially similar to the polyoxyalkylene portion of the associative monomers described above. In one aspect, the polyoxyalkylene portions (ii) include polyoxyethylene, polyoxypropylene, and/or polyoxybutylene units comprising from about 2 to about 150 in one aspect, from about 5 to about 120 in another aspect, and from about 10 to about 60 in a further aspect of ethylene oxide, propylene oxide, and/or butylene oxide units, arranged in random or blocky sequences.

The semi-hydrophobic end group portion (iii) is substantially non-hydrophobic and is selected from hydroxyl and a linear or branched $C_1$ to $C_4$ alkyl.

In one aspect, the semi-hydrophobic monomer can be represented by the following formulas:

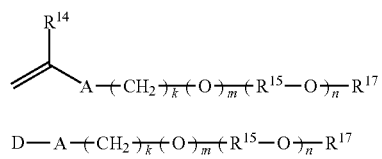

VIII

IX wherein $R^{14}$ is hydrogen or methyl; A is —$CH_2C(O)O$—, —$C(O)O$—, —O—, —$CH_2O$—, —NHC(O)NH—, —C(O)NH—, —Ar—$(CE_2)_z$-NHC(O)O—, —Ar—$(CE_2)_z$-NHC(O)NH—, or —$CH_2CH_2$NHC(O)—; Ar is a divalent arylene (e.g., phenylene); E is H or methyl; z is 0 or 1; k is an integer ranging from about 0 to about 30, and m is 0 or 1, with the proviso that when k is 0, m is 0, and when k is in the range of 1 to about 30, m is 1; $(R^{15}$—$O)_n$ is a polyoxyalkylene moiety, which can be a homopolymer, a random copolymer, or a block copolymer of $C_2$-$C_4$ oxyalkylene units, $R^{15}$ is a divalent alkylene moiety selected from $C_2H_4$, $C_3H_6$, or $C_4H_8$, and combinations thereof; and n is an integer in the range of about 2 to about 150 in one aspect, from about 5 to about 120 in another aspect, and from about 10 to about 60 in a further aspect; $R^{17}$ is selected from hydrogen and a linear or branched $C_1$-$C_4$ alkyl group (e.g., methyl, ethyl, propyl, iso-propyl, butyl, iso-butyl, and tert-butyl); and D represents a vinyl or an allyl moiety.

In one aspect, the semi-hydrophobic monomer under formula VIII can be represented by the following formulas:

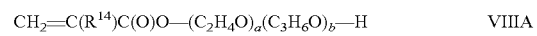 VIIIA

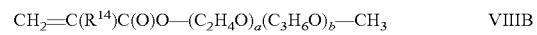 VIIIB wherein $R^{14}$ is hydrogen or methyl, and "a" is an integer ranging from 0 or 2 to about 120 in one aspect, from about 5 to about 45 in another aspect, and from about 10 to about 0.25 in a further aspect, and "b" is an integer ranging from about 0 or 2 to about 120 in one aspect, from about 5 to about 45 in another aspect, and from about 10 to about 0.25 in a further aspect, subject to the proviso that "a" and "b" cannot be 0 at the same time.

Examples of semi-hydrophobic monomers under formula VIIIA include polyethyleneglycol methacrylate available under the product names Blemmer® PE-90 ($R^{14}$=methyl, a=2, b=0), PE-200 ($R^{14}$=methyl, a=4.5, b=0), and PE-350 ($R^{14}$=methyl a=8, b=0); polypropylene glycol methacrylate available under the product names Blemmer® PP-1000 ($R^{14}$=methyl, b=4-6, a=0), PP-500 ($R^{14}$=methyl, a=0, b=9), PP-800 ($R^{14}$=methyl, a=0, b=13); polyethyleneglycol polypropylene glycol methacrylate available under the product names Blemmer® 50PEP-300 ($R^{14}$=methyl, a=3.5, b=2.5), 70PEP-350B ($R^{14}$=methyl, a=5, b=2); polyethyleneglycol acrylate available under the product names Blemmer® AE-90 ($R^{14}$=hydrogen, a=2, b=0), AE-200 ($R^{14}$=hydrogen, a=2, b=4.5), AE-400 ($R^{14}$=hydrogen, a=10, b=0); polypropyleneglycol acrylate available under the product names Blemmer® AP-150 ($R^{14}$=hydrogen, a=0, b=3), AP-400 ($R^{14}$=hydrogen, a=0, b=6), AP-550 ($R^{14}$=hydrogen, a=0, b=9). Blemmer® is a trademark of NOF Corporation, Tokyo, Japan.

Examples of semi-hydrophobic monomers under formula VIIIB include methoxypolyethyleneglycol methacrylate available under the product names Visiomer® MPEG 750 MA W ($R^{14}$=methyl, a=17, b=0), MPEG 1005 MA W ($R^{14}$=methyl, a=22, b=0), MPEG 2005 MA W ($R^{14}$=methyl, a=45, b=0), and MPEG 5005 MA W ($R^{14}$=methyl, a=113, b=0) from Evonik Röhm GmbH, Darmstadt, Germany); Bisomer® MPEG 350 MA ($R^{14}$=methyl, a=8, b=0), and MPEG 550 MA ($R^{14}$=methyl, a=12, b=0) from GEO Specialty Chemicals, Ambler Pa.; Blemmer® PME-100 ($R^{14}$=methyl, a=2, b=0), PME-200 ($R^{14}$=methyl, a=4, b=0), PME400 ($R^{14}$=methyl, a=9, b=0), PME-1000 ($R^{14}$=methyl, a=23, b=0), PME-4000 ($R^{14}$=methyl, a=90, b=0).

In one aspect, the semi-hydrophobic monomer set forth in formula IX can be represented by the following formulas:

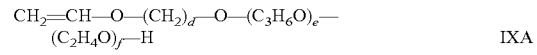 IXA

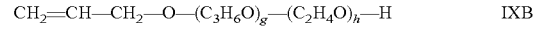 IXB wherein d is an integer of 2, 3, or 4; e is an integer in the range of from about 1 to about 10 in one aspect, from about 2 to about 8 in another aspect, and from about 3 to about 7 in a further aspect; f is an integer in the range of from about 5 to about 50 in one aspect, from about 8 to about 40 in another aspect, and from about 10 to about 30 in a further aspect; g is an integer in the range of from 1 to about 10 in one aspect, from about 2 to about 8 in another aspect, and from about 3 to about 7 in a further aspect; and h is an integer in the range of from about 5 to about 50 in one aspect, and from about 8 to about 40 in another aspect; e, f, g, and h can be 0 subject to the proviso that e and f cannot be 0 at the same time, and g and h cannot be 0 at the same time.

Monomers under formulas IXA and IXB are commercially available under the trade names Emulsogen® R109, R208, R307, RAL109, RAL208, and RAL307 sold by Clariant Corporation; BX-AA-E5P5 sold by Bimax, Inc.; and combinations thereof. EMULSOGEN7 R109 is a randomly ethoxylated/propoxylated 1,4-butanediol vinyl ether having the empirical formula $CH_2=CH-O(CH_2)_4O(C_3H_6O)_4(C_2H_4O)_{10}H$; Emulsogen® R208 is a randomly ethoxylated/propoxylated 1,4-butanediol vinyl ether having the empirical formula $CH_2=CH-O(CH_2)_4O(C_3H_6O)_4(C_2H_4O)_{20}H$; Emulsogen® R307 is a randomly ethoxylated/propoxylated 1,4-butanediol vinyl ether having the empirical formula $CH_2=CH-O(CH_2)_4O(C_3H_6O)_4(C_2H_4O)_{30}H$; Emulsogen® RAL109 is a randomly ethoxylated/propoxylated allyl ether having the empirical formula $CH_2=CHCH_2O(C_3H_6O)_4(C_2H_4O)_{10}H$; Emulsogen® RAL208 is a randomly ethoxylated/propoxylated allyl ether having the empirical formula $CH_2=CHCH_2O(C_3H_6O)_4(C_2H_4O)_{20}H$; Emulsogen® RAL307 is a randomly ethoxylated/propoxylated allyl ether having the empirical formula $CH_2=CHCH_2O(C_3H_6O)_4(C_2H_4O)_{30}H$; and BX-AA-E5P5 is a randomly ethoxylated/propoxylated allyl ether having the empirical formula $CH_2=CHCH_2O(C_3H_6O)_5(C_2H_4O)_5H$.

In the associative and semi-hydrophobic monomers of the invention, the polyoxyalkylene mid-section portion contained in these monomers can be utilized to tailor the hydrophilicity and/or hydrophobicity of the polymers in which they are included. For example, mid-section portions rich in ethylene oxide moieites are more hydrophilic while mid-section portions rich in propylene oxide moieties are more hydrophobic. By adjusting the relative amounts of ethylene oxide to propylene oxide moieties present in these monomers the hydrophilic and hydrophobic properties of the polymers in which these monomers are included can be tailored as desired.

The amount of associative and/or semi-hydrophobic monomer utilized in the preparation of the polymers of the present invention can vary widely and depends, among other things, on the final rheological and aesthetic properties desired in the polymer. When utilized, the monomer reaction mixture contains one or more monomers selected from the associative and/or semi-hydrophobic monomers disclosed above in amounts ranging from about 0.01 to about 15 wt. % in one aspect, from about 0.1 wt. % to about 10 wt. % in another aspect, from about 0.5 to about 8 wt. % in still another aspect and from about 1, 2 or 3 to about 5 wt. % in a further aspect, based on the weight of the total monomers.

Ionizable Monomer

In one aspect of the invention, the crosslinked, nonionic, amphiphilic polymer compositions of the invention can be polymerized from a monomer composition comprising 0 to 5 wt. % of an ionizable and/or ionized monomer, based on the weight of the total monomers, so long as the yield stress value of the yield stress fluids in which the polymers of the invention are included are not deleteriously affected (i.e., the yield stress value of the fluid does not fall below 0.1 Pa).

In another aspect, the amphiphilic polymer compositions of the invention can be polymerized from a monomer composition comprising less than 3 wt. % in one aspect, less than 1 wt. % in a further aspect, less than 0.5 wt. % in a still further aspect, less than 0.1 wt. % in an additional aspect, and less than 0.05 wt. % in a further aspect, of an ionizable and/or an ionized moiety, based on the weight of the total monomers.

Ionizable monomers include monomers having a base neutralizable moiety and monomers having an acid neutralizable moiety. Base neutralizable monomers include olefinically unsaturated monocarboxylic and dicarboxylic acids and their salts containing 3 to 5 carbon atoms and anhydrides thereof. Examples include (meth)acrylic acid, itaconic acid, maleic acid, maleic anhydride, and combinations thereof. Other acidic monomers include styrenesulfonic acid, 2-acrylamido-2-methylpropanesulfonic acid (AMPS® monomer available from Lubrizol Advanced Materials, Inc.), vinylsulfonic acid, vinylphosphonic acid, allylsulfonic acid, methallylsulfonic acid; and salts thereof.

Acid neutralizable monomers include olefinically unsaturated monomers which contain a basic nitrogen atom capable of forming a salt or a quaternized moiety upon the addition of an acid. For example, these monomers include vinylpyridine, vinylpiperidine, vinylimidazole, vinylmethylimidazole, dimethylaminomethyl (meth)acrylate, dimethylaminoethyl (meth)acrylate, diethylaminomethyl (meth)acrylate, dimethylaminoneopentyl (meth)acrylate, dimethylaminopropyl (meth)acrylate, and diethylaminoethyl (meth)acrylate.

Crosslinking Monomer

In one embodiment, the crosslinked, nonionic, amphiphilic polymers useful in the practice of the invention are polymerized from a monomer composition comprising a first monomer comprising at least one nonionic, hydrophilic unsaturated monomer, at least one nonionic, unsaturated hydrophobic monomer, and mixtures thereof, and a third monomer comprising at least one polyunsaturated crosslinking monomer. The component monomers in the polymerizable monomer composition can be present in any weight ratio.

A crosslinking monomer(s) is utilized to polymerize covalent crosslinks into the polymer backbone. In one aspect, the crosslinking monomer is a polyunsaturated compound containing at least 2 unsaturated moieties. In another aspect, the crosslinking monomer contains at least 3 unsaturated moieties. Exemplary polyunsaturated compounds include di(meth)acrylate compounds such as ethylene glycol di(meth)acrylate, polyethylene glycol di(meth)acrylate, triethylene glycol di(meth)acrylate, 1,3-butylene glycol di(meth)acrylate, 1,6-butylene glycol di(meth)acrylate, 1,6-hexanediol di(meth)acrylate, neopentyl glycol di(meth)acrylate, 1,9-nonanediol di(meth)acrylate, 2,2'-bis(4-(acryloxy-propyloxyphenyl))propane, and 2,2'-bis(4-(acryloxydiethoxy-phenyWpropane; tri(meth)acrylate compounds such as, trimethylolpropane tri(meth)acrylate, trimethylolethane tri(meth)acrylate, and tetramethylolmethane tri(meth)acrylate; tetra(meth)acrylate compounds such as ditrimethylolpropane tetra(meth)acrylate, tetramethylolmethane tetra(meth)acrylate, and pentaerythritol tetra(meth)acrylate; hexa(meth)acrylate compounds such as dipentaerythritol hexa(meth)acrylate; allyl compounds such as allyl (meth)acrylate, diallylphthalate, diallyl itaconate, diallyl fumarate, and diallyl maleate; polyallyl ethers of sucrose having from 2 to 8 allyl groups per molecule, polyallyl ethers of pentaerythritol such as pentaerythritol diallyl ether, pentaerythritol triallyl ether, and pentaerythritol tetraallyl ether, and combinations thereof; polyallyl ethers of trimethylolpropane such as trimethylolpropane diallyl ether, trimethylolpropane triallyl ether, and combinations thereof.

Other suitable polyunsaturated compounds include divinyl glycol, divinyl benzene, and methylenebisacrylamide.

In another aspect, suitable polyunsaturated monomers can be synthesized via an esterification reaction of a polyol made from ethylene oxide or propylene oxide or combinations thereof with unsaturated anhydride such as maleic anhydride, citraconic anhydride, itaconic anhydride, or an addition reaction with unsaturated isocyanate such as 3-isopropenyl-α-α-dimethylbenzene isocyanate.

Mixtures of two or more of the foregoing polyunsaturated compounds can also be utilized to crosslink the nonionic, amphiphilic polymers of the invention. In one aspect, the mixture of unsaturated crosslinking monomer contains an average of 2 unsaturated moieties. In another aspect, the mixture of crosslinking monomers contains an average of 2.5 unsaturated moieties. In still another aspect, the mixture of crosslinking monomers contains an average of about 3 unsaturated moieties. In a further aspect, the mixture of crosslinking monomers contains an average of about 3.5 unsaturated moieties.

In one embodiment of the invention, the crosslinking monomer component can be used in an amount ranging from about 0.01 to about 1 wt. % in one aspect, from about 0.05 to about 0.75 wt. % in another aspect, and from about 0.1 to about 0.5 wt. % in a further aspect, based on the dry weight of the nonionic, amphiphilic polymer of the invention.

In another embodiment of the invention, the crosslinking monomer component contains an average of about 3 unsaturated moieties and can be used in an amount ranging from about 0.01 to about 0.3 wt. % in one aspect, from about 0.02 to about 0.25 wt. % in another aspect, from about 0.05 to about 0.2 wt. % in a further aspect, and from about 0.075 to about 0.175 wt. % in a still further aspect, and from about 0.1 to about 0.15 wt. % in another aspect, based upon the total weight of the, nonionic, amphiphilic polymer of the invention.

In one aspect, the crosslinking monomer is selected from trimethylolpropane tri(meth)acrylate, trimethylolethane tri(meth)acrylate, tetramethylolmethane tri(meth)acrylate, pentaerythritol triallylether and polyallyl ethers of sucrose having 3 allyl groups per molecule.

Amphiphilic Polymer Synthesis

The crosslinked, nonionic, amphiphilic polymer of the present invention can be made using conventional free-radical polymerization techniques. The polymerization processes are carried out in the absence of oxygen under an inert atmosphere such as nitrogen. In one aspect, dispersion polymerization techniques are employed to obtain the polymers of the invention. The polymerization can be carried out in any suitable solvent system such as in a hydrocarbon solvent, an organic solvent, as well as in mixtures thereof. The polymerization reactions are initiated by any means which results in the generation of a suitable free-radical. Thermally derived radicals, in which the radical species is generated from thermal, homolytic dissociation of peroxides, hydroperoxides, persulfates, percarbonates, peroxyesters, hydrogen peroxide and azo compounds can be utilized. The initiators can be water soluble or water insoluble depending on the solvent system employed for the polymerization reaction. The initiator compounds can be utilized in an amount of up to 30 wt. % in one aspect, 0.01 to 10 wt. % in another aspect, and 0.2 to 3 wt. % in a further aspect, based on the dry weight of polymer.

Exemplary free radical water soluble initiators include, but are not limited to, inorganic persulfate compounds, such as ammonium persulfate, potassium persulfate, and sodium persulfate; peroxides such as hydrogen peroxide, benzoyl peroxide, acetyl peroxide, and lauryl peroxide; organic hydroperoxides, such as cumene hydroperoxide and t-butyl hydroperoxide; organic peracids, such as peracetic acid, and water soluble azo compounds, such as 2,2'-azobis(2-(tert-alkyl) compounds having a water solubilizing substituent on the alkyl group. Exemplary free radical oil soluble compounds include, but are not limited to 2,2'-azobisisobutyronitrile, and the like. The peroxides and peracids can optionally be activated with reducing agents, such as sodium disulfite, sodium formaldehyde, or ascorbic acid, transition metals, hydrazine, and the like.

In one aspect, azo polymerization catalysts include the Vazo® free-radical polymerization initiators, available from DuPont, such as Vazo® 44 (2,2'-azobis(2-(4,5-dihydroimidazolyl)propane), Vazo® 56 (2,2'-azobis(2-methylpropionamidine) dihydrochloride), Vazo® 67 (2,2'-azobis(2-methylbutyronitrile)), and Vazo® 68 (4,4'-azobis(4-cyanovaleric acid)).

Optionally, the use of known redox initiator systems as polymerization initiators can be employed. Such redox initiator systems include an oxidant (intiator) and a reductant. Suitable oxidants include, for example, hydrogen peroxide, sodium peroxide, potassium peroxide, t-butyl hydroperoxide, t-amyl hydroperoxide, cumene hydroperoxide, sodium perborate, perphosphoric acid and salts thereof, potassium permanganate, and ammonium or alkali metal salts of peroxydisulfuric acid, typically at a level of 0.01% to 3.0% by weight, based on dry polymer weight, are used. Suitable reductants include, for example, alkali metal and ammonium salts of sulfur-containing acids, such as sodium sulfite, bisulfite, thiosulfate, hydrosulfite, sulfide, hydrosulfide or dithionite, formadinesulfinic acid, hydroxymethanesulfonic acid, acetone bisulfite, amines such as ethanolamine, glycolic acid, glyoxylic acid hydrate, ascorbic acid, isoascorbic acid, lactic acid, glyceric acid, malic acid, 2-hydroxy-2-sulfinatoacetic acid, tartaric acid and salts of the preceding acids typically at a level of 0.01% to 3.0% by weight, based on dry polymer weight, is used. In one aspect, combinations of peroxydisulfates with alkali metal or ammonium bisulfites can be used, for example, ammonium peroxydisulfate and ammonium bisulfite. In another aspect, combinations of hydrogen peroxide containing compounds (t-butyl hydroperoxide) as the oxidant with ascorbic or erythorbic acid as the reductant can be utilized. The ratio of peroxide-containing compound to redox reductant is within the range from 30:1 to 0.05:1.

Examples of suitable hydrocarbon solvents or diluents that can be utilized in the polymerization medium are aromatic solvents such as toluene, o-xylene, p-xylene, cumene, chlorobenzene, and ethylbenzene, aliphatic hydrocarbons, such as pentane, hexane, heptane, octane, nonane, decane, and the like, halogenated hydrocarbons, such as methylene chloride, alicyclic hydrocarbons, such as cyclopentane, methyl cyclopentane, cyclohexane, cycloheptane, cyclooctane, cyclononane, cyclodecane, and the like, and mixtures thereof. Suitable organic solvents include acetone, cyclohexanone, tetrahydrofuran, dioxane, glycols and glycol derivatives, polyalkylene glycols and derivatives thereof, diethyl ether, tert-butyl methyl ether, methyl acetate, ethyl acetate, propyl acetate, isopropyl acetate, butyl acetate, butyl propionate, and mixtures thereof. Mixtures of hydrocarbon solvents and organic solvents are also useful.

In the dispersion polymerization process, it can be advantageous to stabilize the monomer/polymer droplets or particles by means of surface active auxiliaries. Typically, these are emulsifiers, protective colloids or dispersion stabilizing polymers. The surface active auxiliaries used can be anionic, nonionic, cationic or amphoteric. Examples of anionic emulsifiers are alkylbenzenesulfonic acids, sulfonated fatty acids, sulfosuccinates, fatty alcohol sulfates, alkylphenol sulfates and fatty alcohol ether sulfates. Examples of usable nonionic emulsifiers are alkylphenol ethoxylates, primary alcohol ethoxylates, fatty acid ethoxylates, alkanolamide ethoxylates, fatty amine ethoxylates, EO/PO block copolymers and alkylpolyglucosides. Examples of cationic and amphoteric emulsifiers used are quaternized amine alkoxylates, alkylbetaines, alkylamidobetaines and sulfobetaines.

Examples of typical protective colloids are cellulose derivatives, polyethylene glycol, polypropylene glycol, copolymers of ethylene glycol and propylene glycol, polyvinyl acetate, poly(vinyl alcohol), partially hydrolyzed poly (vinyl alcohol), polyvinyl ether, starch and starch derivatives, dextran, polyvinylpyrrolidone, polyvinylpyridine, polyethyleneimine, polyvinylimidazole, polyvinylsuccinimide, polyvinyl-2-methylsuccinimide, polyvinyl-1,3-oxazolid-2-one, polyvinyl-2-methylimidazoline and maleic acid or anhydride copolymers. The emulsifiers or protective colloids are customarily used in concentrations from 0.05 to 20 wt. %, based on the weight of the total monomers.

The polymerization reaction can be carried out at temperatures ranging from 20 to 200° C. in one aspect, from 50 to 150° C. in another aspect, and from 60 to 100° C. in a further aspect.

The polymerization can be carried out the presence of chain transfer agents. Suitable chain transfer agents include, but are not limited to, thio- and disulfide containing compounds, such as $C_1$-$C_{18}$ alkyl mercaptans, such as tert-butyl mercaptan, n-octyl mercaptan, n-dodecyl mercaptan, tert-dodecyl mercaptan hexadecyl mercaptan, octadecyl mercaptan; mercaptoalcohols, such as 2-mercaptoethanol, 2-mercaptopropanol; mercaptocarboxylic acids, such as mercaptoacetic acid and 3-mercaptopropionic acid; mercaptocarboxylic acid esters, such as butyl thioglycolate, isooctyl thioglycolate, dodecyl thioglycolate, isooctyl 3-mercaptopropionate, and butyl 3-mercaptopropionate; thioesters; $C_1$-$C_{18}$ alkyl disulfides; aryldisulfides; polyfunctional thiols such as trimethylolpropane-tris-(3-mercaptopropionate), pentaerythritol-tetra-(3-mercaptopropionate), pentaerythritol-tetra-(thioglycolate), pentaerythritol-tetra-(thiolactate), dipentaerythritol-hexa-(thioglycolate), and the like; phosphites and hypophosphites; $C_1$-$C_4$ aldehydes, such as formaldehyde, acetaldehyde, propionaldehyde; haloalkyl compounds, such as carbon tetrachloride, bromotrichloromethane, and the like; hydroxylammonium salts such as hydroxylammonium sulfate; formic acid; sodium bisulfite; isopropanol; catalytic chain transfer agents such as, for example, cobalt complexes (e.g., cobalt (II) chelates).

The chain transfer agents are generally used in amounts ranging from 0.1 to 10 wt. %, based on the total weight of the monomers present in the polymerization medium.

Dispersion Process

In another aspect of the invention, the crosslinked, nonionic, amphiphilic polymer is obtained by free-radical mediated dispersion polymerization in a non-aqueous medium that is a solvent for the monomers but a substantially non-solvent for the resulting polymers. Non-aqueous dispersion polymerization is discussed in detail in the book *Dispersion Polymerization in Organic Media*, edited by K. E. G. Barrett and published by John Wiley & Sons, New York, 1975. In a typical procedure for preparing a dispersion polymer, an organic solvent containing the polymerizable monomers, any polymerization additives such as processing aids, chelants, pH buffers and a stabilizer polymer is charged to an oxygen purged, temperature controlled reactor equipped with a mixer, a thermocouple, a nitrogen purging tube, and a reflux condenser. The reaction medium is mixed vigorously, heated to the desired temperature, and then a free-radical initiator is added. The polymerization is usually conducted at reflux temperature to prevent oxygen from inhibiting the reaction. Reflux temperature typically falls in the range of from about 40° C. to about 200° C. in one aspect, and from about 60° C. to about 140° C. in another aspect, depending on the boiling point of the solvents comprising the non-aqueous medium in which the polymer is prepared. The reaction medium is continually purged with nitrogen while maintaining temperature and mixing for several hours. After this time, the mixture is cooled to room temperature, and any post-polymerization additives are charged to the reactor. Hydrocarbons are preferably used as the dispersion solvent. The reaction time required in such a polymerization will vary with the reaction temperature employed, initiator system, and initiator level. Generally, this reaction time will vary from about 20 minutes up to about 30 hours. Commonly, it will be preferred to utilize a reaction time from about 1 up to about 6 hours.

Typically, polymerization of the monomers used to prepare the polymers is initiated by free-radical initiators that are soluble in the non-aqueous medium. Examples include azo compound initiators such as 2,2'-azobis(2,4-dimethylpentane nitrile), 2,2'-azobis(2-methylbutanenitrile), and 2,2'-azobis(2-methylbutyronitrile). The initiators can be used in customary amounts, for example 0.05 to 7 wt. %, based on the amount of monomers to be polymerized.

In one aspect, the solvent is a hydrocarbon selected from aliphatic and cycloaliphatic solvents, as well as mixtures thereof. Exemplary hydrocarbon solvents include pentane, hexane, heptane, octane, nonane, decane, cyclopentane, methyl cyclopentane, cyclohexane, cycloheptane, cyclooctane, cyclononane, cyclodecane, and their mixtures.

In another aspect, the solvent is an organic solvent selected from acetone, cyclohexanone, tetrahydrofuran, dioxane, glycols and glycol derivatives, polyalkylene glycols and derivatives thereof, diethyl ether, tert-butyl methyl ether, methyl acetate, methyl acetate, ethyl acetate, propyl acetate, isopropyl acetate, butyl acetate, butyl propionate, ethanol, isopropanol, water, and mixtures thereof.

The amount of solvent utilized normally will be in excess of the monomers to be polymerized and the proportion can vary from at least 1 wt. % of the monomer components and 99 wt. % solvent, up to about 65 wt. % polymerizable monomer components and 35 wt. % solvent. In another aspect, a concentration of about 10 to 60 wt. % polymerizable monomer components can be employed, where the weight percent is based on the total amount of monomer and solvent charged to the reaction vessel.

When mixtures of organic solvents and hydrocarbon solvents are utilized, the organic solvents and the hydrocarbon solvents can be premixed or can be added separately to the reaction mixture and the polymerization reaction can be carried out thereafter. The relative weight ratio of the at least one organic solvent to the at least one hydrocarbon solvent can be in the range of from about 95/5 to about 1/99 in one aspect, from about 80/20 to about 5/95 in another aspect, and from about 2:1 to 1:2 in a further aspect.

The stabilizer, typically a block or graft copolymer, prevents settling of the desired solid polymer product produced during the reaction. The block copolymer dispersion stabilizer can be selected from a variety of polymers containing at least two blocks wherein at least one of said blocks ("A" block) is soluble in the dispersion medium and at least another of said blocks ("B" block) is insoluble in the dispersion medium, and the stabilizer acts to disperse polymer products which are formed in the stabilizer's presence. The insoluble "B" block provides an anchor segment for attachment to the obtained polymer product, thus reducing the solubility of the polymerized product in the dispersion medium. The soluble "A" block of the dispersion stabilizer provides a sheath around the otherwise insoluble polymer and maintains the polymeric product as numerous small discrete particles rather than an agglomerated or highly coalesced mass. Details of the mechanism of such steric stabilization are described in Napper, D. H., "Polymeric Stabilization of Colloidal Dispersions," Academic Press, New York, N.Y., 1983. Representative stabilizers useful in the dispersion polymerization process of the invention are disclosed in U.S. Pat. Nos. 4,375,533; 4,419,502; 4,526,937; 4,692,502; 5,288,814; 5,349,030; 5,373,044; 5,468,797; and 6,538,067, which are incorporated herein by reference.

In one aspect of the invention, the steric stabilizer is selected from poly(12-hydroxystearic acid) such as disclosed in U.S. Pat. No. 5,288,814. In another aspect of the invention, the steric stabilizer comprises the ester of the reaction product of a $C_{18}$—$O_{24}$ hydrocarbyl substituted succinic acid or the anhydride thereof with a polyol such as disclosed in U.S. Pat. No. 7,044,988. In another aspect, the steric stabilizer comprises the ester of the reaction product of a $C_{20}$ to $C_{24}$ alkyl substituted succinic anhydride and a polyol selected from glycerin and/or a polyglycerol containing 2 to 6 glycerin units. U.S. Pat. Nos. 5,288,814 and 7,044,988 are herein incorporated by reference.

In still another aspect, the steric stabilizer is a copolymer of N-vinyl pyrrolidone/stearyl methacrylate/butyl acrylate. In one aspect the comonomers are incorporated into the stabilizer polymer in a weight ratio of 50/30/20, respectively. Mixtures of this steric stabilizer with esters and half esters of the reaction product of the $C_{12}$ to $C_{30}$ alkenyl substituted succinic anhydride and a polyol selected from $C_2$ to $C_4$ glycols are also contemplated.

The amount of steric stabilizer used in the polymerization process of this invention will cause variations in the size and specific surface area of the disperse polymer. In general, the amount of stabilizer utilized can range from 0.1 to 10 wt. % of the monomers present in the main polymerization process. Of course, smaller particles of disperse polymer require more stabilizer than large particles of disperse polymer.

In one aspect, the crosslinked, nonionic, amphiphilic polymers of the invention are selected from a dispersion polymer polymerized from a monomer mixture comprising 95 to 99.5 wt. % of a combination of at least one vinyl lactam and at least one vinyl ester of a $C_1$-$C_{22}$ carboxylic acid, wherein at least 60 wt. % of said monomer combination is selected from a vinyl lactam, 0.05 to 5 wt. % of at least one $C_8$-$C_{22}$ alkyl (meth)acrylate, optionally up to 5 wt. % of hydrophobically modified alkoxylated associative and/or a semi-hydrophobic monomer (said weight percent is based on the weight of the total monomers), and 0.01 to 1 wt. % of a crosslinking monomer (based on the weight of the dry polymer). When the optional associative and/or semi-hydrophobic monomer is present, the combined weight percentage of the $C_8$-$C_{22}$ alkyl (meth)acrylate and the associative and/or semi-hydrophobic monomer cannot exceed 5 wt. % of the weight of the total monomer composition.

In another embodiment, the crosslinked, nonionic, amphiphilic dispersion polymer is polymerized from a monomer mixture comprising 60 to 90 wt. % of N-vinyl pyrrolidone, 10 to 35 wt. % of at least one vinyl ester selected from vinyl acetate, vinyl propionate, vinyl butyrate, vinyl isobutyrate, vinyl valerate, vinyl hexanoate, vinyl 2-methylhexanate, vinyl 2-ethylhexanoate, vinyl iso-octanoate, vinyl nonanoate, vinyl neodecanoate, vinyl decanoate, vinyl versatate, vinyl laurate, vinyl palmitate, and vinyl stearate, 0.5 to 5 wt. % of an $C_8$-$C_{22}$ alkyl (meth)acrylate selected from octyl (meth)acrylate, 2-ethylhexyl (meth)acrylate, decyl (meth)acrylate, isodecyl (meth)acrylate, lauryl (meth)acrylate, tetradecyl (meth)acrylate, hexadecyl (meth)acrylate, stearyl (meth)acrylate, and behenyl (meth)acrylate, 0 to 4.5 wt. % of at least one associative monomer and/or semi-hydrophobic monomer (said weight percent is based on the weight of the total monomers), and 0.01 to 1 wt. % of a crosslinking monomer (based on the weight of the dry polymer). When the optional hydrophobically modified ethoxylated (meth)acrylate is present the combined weight percentage of the $C_8$-$C_{22}$ alkyl (meth)acrylate and the associative monomer and/or the semi-hydrophobic monomer cannot exceed 5 wt. % of the weight of the total monomer composition.

Yield Stress Fluids

In one exemplary aspect of the invention, the yield stress fluid of the invention comprises: i) at least one crosslinked, nonionic amphiphilic polymer(s) described previously; ii) at least one surfactant selected from at least one anionic surfactant, at least one cationic surfactant, at least one amphoteric surfactant, at least one nonionic surfactant, and combinations thereof; and iii) water.

In another exemplary aspect of the invention, the yield stress fluid of the invention comprises: i) at least one crosslinked, nonionic amphiphilic polymer(s) described previously; ii) at least one anionic surfactant; and iii) water.

In another exemplary aspect of the invention, the yield stress fluid of the invention comprises: i) at least one crosslinked, nonionic amphiphilic polymer(s) described previously; ii) at least one anionic surfactant and at least one amphoteric surfactant; and iii) water.

Surprisingly, the present amphiphilic polymers can be activated by a surfactant to provide a stable yield stress fluid with desirable rheological and aesthetic properties with the ability to suspend particulate and insoluble materials in an aqueous medium for indefinite periods of time independent of pH. The yield stress value, elastic modulus and optical clarity are substantially independent of pH in the compositions in which they are included. The yield stress fluid of the invention is useful in the pH range of from about 2 to about 14 in one aspect, from about 3 to 11 in another aspect, and from about 4 to about 9 in a further aspect. Unlike the pH-responsive crosslinked polymers (acid or base sensitive) that require neutralization with an acid or a base to impart a desired rheological profile, the rheological profiles of the crosslinked, nonionic, amphiphilic polymers of the invention are substantially independent of pH. By substantially independent of pH is meant that the yield stress fluid within which the polymer of the invention is included imparts a desired rheological profile (e.g., a yield stress of at least 0.1 Pa in one aspect, at least 0.5 Pa in another aspect, at least 1 Pa in still another aspect, and at least 2 Pa in a further aspect) across a wide pH range (e.g., from about 2 to about 14) wherein the standard deviation in yield stress values across the pH range is less than 1 Pa in one aspect, less than 0.5 Pa in another aspect, and less than 0.25 Pa in a further aspect of the invention.

In one exemplary aspect of the invention, the yield stress fluid comprises at least one crosslinked, nonionic, amphiphilic polymer, at least one anionic surfactant, an optional nonionic surfactant, and water.

In another exemplary aspect, the yield stress fluid comprises at least one crosslinked, nonionic amphiphilic polymer, at least one anionic surfactant, at least one amphoteric surfactant, an optional nonionic surfactant, and water.

In still another exemplary aspect, the yield stress fluid comprises at least one crosslinked, nonionic, amphiphilic polymer, at least one anionic ethoxylated surfactant, an optional nonionic surfactant, and water. In one aspect the average degree of ethoxylation in the anionic surfactant can range from about 1 to about 3. In another aspect the average degree of ethoxylation is about 2.

In a further exemplary aspect, the yield stress fluid comprises at least one crosslinked, nonionic, amphiphilic polymer, at least one anionic ethoxylated surfactant, at least one amphoteric surfactant, an optional nonionic surfactant, and water. In one aspect the average degree of ethoxylation in the anionic surfactant can range from about 1 to about 3. In another aspect the average degree of ethoxylation is about 2.

In a still further exemplary aspect, the yield stress fluid comprises at least one crosslinked, nonionic, amphiphilic polymer, at least one anionic non-ethoxylated surfactant, at least one anionic ethoxylated surfactant, an optional nonionic surfactant, and water. In one aspect the average degree of ethoxylation in the anionic surfactant can range from about 1 to about 3. In another aspect the average degree of ethoxylation is about 2.

In another exemplary aspect, the yield stress fluid comprises at least one crosslinked, nonionic, amphiphilic polymer, at least one anionic non-ethoxylated surfactant, at least one anionic ethoxylated surfactant, at least one amphoteric surfactant, an optional nonionic surfactant, and water. In one aspect the average degree of ethoxylation in the anionic surfactant can range from about 1 to about 3. In another aspect the average degree of ethoxylation is about 2.

The amount of amphiphilic polymer utilized in formulating the yield stress fluid of the invention ranges from about 0.5 to about 5 wt. % polymer solids (100% active polymer) based on the weight of the total composition. In another aspect, the amount of amphiphilic polymer utilized in the formulation ranges from about 0.75 wt. % to about 3.5 wt. %. In still another aspect, the amount of amphiphilic polymer employed in the yield stress fluid ranges from about 1 to about 3 wt. %. In a further aspect, the amount of amphiphilic polymer employed in the yield stress fluid ranges from about 1.5 wt. % to about 2.75 wt. %. In a still further aspect the amount of amphiphilic polymer utilized in the yield stress fluid ranges from about 2 to about 2.5 wt. %. The crosslinked, nonionic, amphiphilic polymer utilized in formulating the yield stress fluids of the invention is a dispersion polymer.

The surfactants utilized to formulate the yield stress fluids of the invention can be selected from anionic surfactants, cationic surfactants, amphoteric surfactants, nonionic surfactants, and mixtures thereof.

Non-limiting examples of anionic surfactants are disclosed in *McCutcheon's Detergents and Emulsifiers*, North American Edition, 1998, published by Allured Publishing Corporation; and McCutcheon's, *Functional Materials*, North American Edition (1992); both of which are incorporated by reference herein in their entirety. The anionic surfactant can be any of the anionic surfactants known or previously used in the art of aqueous surfactant compositions. Suitable anionic surfactants include but are not limited to alkyl sulfates, alkyl ether sulfates, alkyl sulphonates, alkaryl sulfonates, α-olefin-sulphonates, alkylamide sulphonates, alkarylpolyether sulphates, alkylamidoether sulphates, alkyl monoglyceryl ether sulfates, alkyl monoglyceride sulfates, alkyl monoglyceride sulfonates, alkyl succinates, alkyl sulfosuccinates, alkyl sulfosuccinamates, alkyl ether sulphosuccinates, alkyl amidosulfosuccinates; alkyl sulphoacetates, alkyl phosphates, alkyl ether phosphates, alkyl ether carboxylates, alkyl amidoethercarboxylates, N-alkylamino acids, N-acyl amino acids, alkyl peptides, N-acyl taurates, alkyl isethionates, carboxylate salts wherein the acyl group is derived from fatty acids; and the alkali metal, alkaline earth metal, ammonium, amine, and triethanolamine salts thereof.

In one aspect, the cation moiety of the forgoing salts is selected from sodium, potassium, magnesium, ammonium, mono-, di- and triethanolamine salts, and mono-, di-, and tri-isopropylamine salts. The alkyl and acyl groups of the foregoing surfactants contain from about 6 to about 24 carbon atoms in one aspect from 8 to 22 carbon atoms in another aspect and from about 12 to 18 carbon atoms in a further aspect and can be saturated or unsaturated. The aryl groups in the surfactants are selected from phenyl or benzyl. The ether containing surfactants set forth above can contain from 1 to 10 ethylene oxide and/or propylene oxide units per surfactant molecule in one aspect, and from 1 to 3 ethylene oxide units per surfactant molecule in another aspect.

Examples of suitable anionic surfactants include but are not limited to the sodium, potassium, lithium, magnesium, and ammonium salts of laureth sulfate, trideceth sulfate, myreth sulfate, $C_{12}$-$C_{13}$ pareth sulfate, $C_{12}$-$C_{14}$ pareth sulfate, and $C_{12}$-$C_{15}$ pareth sulfate, ethoxylated with 1, 2, 3, 4 or 5 moles of ethylene oxide; sodium, potassium, lithium, magnesium, ammonium, and triethanolamine lauryl sulfate, coco sulfate, tridecyl sulfate, myrstyl sulfate, cetyl sulfate, cetearyl sulfate, stearyl sulfate, oleyl sulfate, and tallow sulfate, disodium lauryl sulfosuccinate, disodium laureth sulfosuccinate, sodium cocoyl isethionate, sodium $C_{12}$-$C_{14}$ olefin sulfonate, sodium laureth-6 carboxylate, sodium methyl cocoyl taurate, sodium cocoyl glycinate, sodium myristyl sarcocinate, sodium dodecylbenzene sulfonate, sodium cocoyl sarcosinate, sodium cocoyl glutamate, potassium myristoyl glutamate, triethanolamine monolauryl phosphate, and fatty acid soaps, including the sodium, potassium, ammonium, and triethanolamine salts of a saturated and unsaturated fatty acids containing from about 8 to about 22 carbon atoms.

The cationic surfactants can be any of the cationic surfactants known or previously used in the art of aqueous surfactant compositions. Useful cationic surfactants can be one or more of those described, for example, in *McCutcheon's Detergents and Emulsifiers*, North American Edition, 1998, supra, and *Kirk-Othmer, Encyclopedia of Chemical Technology*, 4th Ed., Vol. 23, pp. 478-541, the contents of which are herein incorporated by reference. Suitable classes of cationic surfactants include but are not limited to alkyl amines, alkyl imidazolines, ethoxylated amines, quaternary compounds and quaternized esters. In addition, alkyl amine oxides can function as a cationic surfactant at a low pH.

Alkylamine surfactants can be salts of primary, secondary and tertiary fatty $C_{12}$-$C_{22}$ alkylamines, substituted or unsubstituted, and substances sometimes referred to as "amidoamines". Non-limiting examples of alkylamines and salts thereof include dimethyl cocamine, dimethyl palmitamine, dioctylamine, dimethyl stearamine, dimethyl soyamine, soyamine, myristyl amine, tridecyl amine, ethyl stearylamine, N-tallowpropane diamine, ethoxylated stearylamine, dihydroxy ethyl stearylamine, arachidylbehenylamine, dimethyl lauramine, stearylamine hydrochloride, soyamine chloride, stearylamine formate, N-tallowpropane diamine dichloride, and amodimethicone.

Non-limiting examples of amidoamines and salts thereof include stearamido propyl dimethyl amine, stearamidopropyl dimethylamine citrate, palmitamidopropyl diethylamine, and cocamidopropyl dimethylamine lactate.

Non-limiting examples of alkyl imidazoline surfactants include alkyl hydroxyethyl imidazoline, such as stearyl hydroxyethyl imidazoline, coco hydroxyethyl imidazoline, ethyl hydroxymethyl oleyl oxazoline, and the like.

Non-limiting examples of ethyoxylated amines include PEG-cocopolyamine, PEG-15 tallow amine, quaternium-52, and the like.

Among the quaternary ammonium compounds useful as cationic surfactants, some correspond to the general formula: $(R^{20}R^{21}R^{22}R^{23}N^+)E^-$, wherein $R^{20}$, $R^{21}$, $R^{22}$, and $R^{23}$ are independently selected from an aliphatic group having from 1 to about 22 carbon atoms, or an aromatic, alkoxy, polyoxyalkylene, alkylamido, hydroxyalkyl, aryl or alkylaryl group having 1 to about 22 carbon atoms in the alkyl chain; and $E^-$ is a salt-forming anion such as those selected from halogen, (e.g., chloride, bromide), acetate, citrate, lactate, glycolate, phosphate, nitrate, sulfate, and alkylsulfate. The aliphatic groups can contain, in addition to carbon and hydrogen atoms, ether linkages, ester linkages, and other groups such as amino groups. The longer chain aliphatic groups, e.g., those of about 12 carbons, or higher, can be saturated or unsaturated. In one aspect, the aryl groups are selected from phenyl and benzyl.

Exemplary quaternary ammonium surfactants include, but are not limited to cetyl trimethylammonium chloride, cetylpyridinium chloride, dicetyl dimethyl ammonium chloride, dihexadecyl dimethyl ammonium chloride, stearyl dimethyl benzyl ammonium chloride, dioctadecyl dimethyl ammonium chloride, dieicosyl dimethyl ammonium chloride, didocosyl dimethyl ammonium chloride, dihexadecyl dimethyl ammonium chloride, dihexadecyl dimethyl ammonium acetate, behenyl trimethyl ammonium chloride, benzalkonium chloride, benzethonium chloride, and di(coconutalkyl) dimethyl ammonium chloride, ditallowedimethyl ammonium chloride, di(hydrogenated tallow) dimethyl ammonium chloride, di(hydrogenated tallow) dimethyl ammonium acetate, ditallowedimethyl ammonium methyl sulfate, ditallow dipropyl ammonium phosphate, and ditallow dimethyl ammonium nitrate.

Examples of amine oxides include, but are not limited to, dimethyl-dodecylamine oxide, oleyldi(2-hydroxyethyl) amine oxide, dimethyltetradecylamine oxide, di(2-hydroxyethyl)-tetradecylamine oxide, dimethylhexadecylamine oxide, behenamine oxide, cocamine oxide, decyltetradecylamine oxide, dihydroxyethyl $C_{12}$-$C_{15}$ alkoxypropylamine oxide, dihydroxyethyl cocamine oxide, dihydroxyethyl lauramine oxide, dihydroxyethyl stearamine oxide, dihydroxyethyl tallowamine oxide, hydrogenated palm kernel amine oxide, hydrogenated tallowamine oxide, hydroxyethyl hydroxypropyl $C_{12}$-$C_{15}$ alkoxypropylamine oxide, lauramine oxide, myristamine oxide, cetylamine oxide, oleamidopropylamine oxide, oleamine oxide, palmitamine oxide, PEG-3 lauramine oxide, dimethyl lauramine oxide, potassium trisphosphonomethylamine oxide, soyamidopropylamine oxide, cocamidopropylamine oxide, stearamine oxide, tallowamine oxide, and mixtures thereof.

The term "amphoteric surfactant" as used herein, is also intended to encompass zwitterionic surfactants, which are well known to formulators skilled in the art as a subset of amphoteric surfactants. Non-limiting examples of amphoteric surfactants are disclosed in *McCutcheon's Detergents and Emulsifiers*, North American Edition, supra, and McCutcheon's, *Functional Materials*, North American Edition, supra; both of which are incorporated by reference herein in their entirety. Suitable examples include but are not limited to amino acids (e.g., N-alkyl amino acids and N-acyl amino acids), betaines, sultaines, and alkyl amphocarboxylates.

Amino acid based surfactants suitable in the practice of the present invention include surfactants represented by the formula:

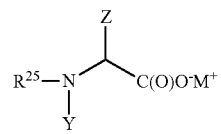

wherein $R^{25}$ represents a saturated or unsaturated hydrocarbon group having 10 to 22 carbon atoms or an acyl group containing a saturated or unsaturated hydrocarbon group having 9 to 22 carbon atoms, Y is hydrogen or methyl, Z is selected from hydrogen, $—CH_3$, $—CH(CH_3)_2$, $—CH_2CH(CH_3)_2$, $—CH(CH_3)CH_2CH_3$, $—CH_2C_6H_5$, $—CH_2C_6H_4OH$, $—CH_2OH$, $—CH(OH)CH_3$, $—(CH_2)_4NH_2$, $—(CH_2)_3NHC(NH)NH_2$, $—CH_2C(O)O^-M^+$, $—(CH_2)_2C(O)O^-M^+$. M is a salt forming cation. In one aspect, $R^{25}$ represents a radical selected from a linear or branched $C_{10}$ to $C_{22}$ alkyl group, a linear or branched $C_{10}$ to $C_{22}$ alkenyl group, an acyl group represented by $R^{26}C(O)—$, wherein $R^{26}$ is selected from a linear or branched $C_9$ to $C_{22}$ alkyl group, a linear or branched $C_9$ to $C_{22}$ alkenyl group. In one aspect, $M^+$ is a cation selected from sodium, potassium, ammonium, and triethanolamine (TEA).

The amino acid surfactants can be derived from the alkylation and acylation of α-amino acids such as, for example, alanine, arginine, aspartic acid, glutamic acid, glycine, isoleucine, leucine, lysine, phenylalanine, serine, tyrosine, and valine. Representative N-acyl amino acid surfactants are, but not limited to the mono- and di-carboxylate salts (e.g., sodium, potassium, ammonium and TEA) of N-acylated glutamic acid, for example, sodium cocoyl glutamate, sodium lauroyl glutamate, sodium myristoyl glutamate, sodium palmitoyl glutamate, sodium stearoyl glutamate, disodium cocoyl glutamate, disodium stearoyl glutamate, potassium cocoyl glutamate, potassium lauroyl glutamate, and potassium myristoyl glutamate; the carboxylate salts (e.g., sodium, potassium, ammonium and TEA) of N-acylated alanine, for example, sodium cocoyl alaninate, and TEA lauroyl alaninate; the carboxylate salts (e.g., sodium, potassium, ammonium and TEA) of N-acylated glycine, for example, sodium cocoyl glycinate, and potassium cocoyl glycinate; the carboxylate salts (e.g., sodium, potassium, ammonium and TEA) of N-acylated sarcosine, for example, sodium lauroyl sarcosinate, sodium cocoyl sarcosinate, sodium myristoyl sarcosinate, sodium oleoyl sarcosinate, and ammonium lauroyl sarcosinate; and mixtures of the foregoing surfactants.

The betaines and sultaines useful in the present invention are selected from alkyl betaines, alkylamino betaines, and alkylamido betaines, as well as the corresponding sulfobetaines (sultaines) represented by the formulas:

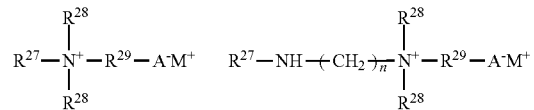

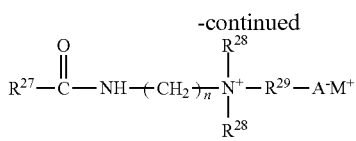

wherein $R^{27}$ is a $C_7$-$C_{22}$ alkyl or alkenyl group, each $R^{28}$ independently is a $C_1$-$C_4$ alkyl group, $R^{29}$ is a $C_1$-$C_5$ alkylene group or a hydroxy substituted $C_1$-$C_5$ alkylene group, n is an integer from 2 to 6, A is a carboxylate or sulfonate group, and M is a salt forming cation. In one aspect, $R^{27}$ is a $C_{11}$-$C_{18}$ alkyl group or a $C_{11}$-$C_{18}$ alkenyl group. In one aspect, $R^{28}$ is methyl. In one aspect, $R^{29}$ is methylene, ethylene or hydroxy propylene. In one aspect, n is 3. In a further aspect, M is selected from sodium, potassium, magnesium, ammonium, and mono-, di- and triethanolamine cations.

Examples of suitable betaines include, but are not limited to, lauryl betaine, coco betaine, oleyl betaine, cocohexadecyl dimethylbetaine, lauryl amidopropyl betaine, cocoamidopropyl betaine (CAPB), and cocamidopropyl hydroxysultaine.

The alkylamphocarboxylates such as the alkylamphoacetates and alkylamphopropionates (mono- and disubstituted carboxylates) can be represented by the formula:

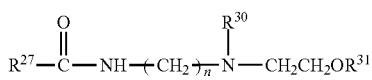

wherein $R^{27}$ is a $C_7$-$C_{22}$ alkyl or alkenyl group, $R^{30}$ is —$CH_2C(O)O^-M^+$, —$CH_2CH_2C(O)O^-M^+$, or —$CH_2CH(OH)CH_2SO_3^-M^+$, $R^{31}$ is hydrogen or —$CH_2C(O)O^-M^+$, and M is a cation selected from sodium, potassium, magnesium, ammonium, and mono-, di- and triethanolamine.

Exemplary alkylamphocarboxylates include, but are not limited to, sodium cocoamphoacetate, sodium lauroamphoacetate, sodium capryloamphoacetate, disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, and disodium capryloamphodipropionate.

Non-limiting examples of nonionic surfactants are disclosed in *McCutcheon's Detergents and Emulsifiers*, North American Edition, 1998, supra; and McCutcheon's, *Functional Materials*, North American, supra; both of which are incorporated by reference herein in their entirety. Additional Examples of nonionic surfactants are described in U.S. Pat. No. 4,285,841, to Barrat et al., and U.S. Pat. No. 4,284,532, to Leikhim et al., both of which are incorporated by reference herein in their entirety. Nonionic surfactants typically have a hydrophobic portion, such as a long chain alkyl group or an alkylated aryl group, and a hydrophilic portion containing various degrees of ethoxylation and/or propoxylation (e.g., 1 to about 50) ethoxy and/or propoxy moieties. Examples of some classes of nonionic surfactants that can be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty acids, condensation products of ethylene oxide with long chain amines or amides, condensation products of ethylene oxide with alcohols, and mixtures thereof.

Suitable nonionic surfactants include, for example, alkyl polysaccharides, alcohol ethoxylates, block copolymers, castor oil ethoxylates, ceto/oleyl alcohol ethoxylates, cetearyl alcohol ethoxylates, decyl alcohol ethoxylates, dinonyl phenol ethoxylates, dodecyl phenol ethoxylates, end-capped ethoxylates, ether amine derivatives, ethoxylated alkanolamides, ethylene glycol esters, fatty acid alkanolamides, fatty alcohol alkoxylates, lauryl alcohol ethoxylates, monobranched alcohol ethoxylates, nonyl phenol ethoxylates, octyl phenol ethoxylates, oleyl amine ethoxylates, random copolymer alkoxylates, sorbitan ester ethoxylates, stearic acid ethoxylates, stearyl amine ethoxylates, tallow oil fatty acid ethoxylates, tallow amine ethoxylates, tridecanol ethoxylates, acetylenic diols, polyoxyethylene sorbitols, and mixtures thereof. Various specific examples of suitable nonionic surfactants include, but are not limited to, methyl gluceth-10, PEG-20 methyl glucose distearate, PEG-20 methyl glucose sesquistearate, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxyethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, laureth-2, laureth-3, laureth-4, PEG-3 castor oil, PEG 600 dioleate, PEG 400 dioleate, poloxamers such as poloxamer 188, polysorbate 21, polysorbate 40, polysorbate 60, polysorbate 61, polysorbate 65, polysorbate 80, polysorbate 81, polysorbate 85, sorbitan caprylate, sorbitan cocoate, sorbitan diisostearate, sorbitan dioleate, sorbitan distearate, sorbitan fatty acid ester, sorbitan isostearate, sorbitan laurate, sorbitan oleate, sorbitan palmitate, sorbitan sesquiisostearate, sorbitan sesquioleate, sorbitan sesquistearate, sorbitan stearate, sorbitan triisostearate, sorbitan trioleate, sorbitan tristearate, sorbitan undecylenate, or mixtures thereof.

Alkyl glycoside nonionic surfactants can also be employed and are generally prepared by reacting a monosaccharide, or a compound hydrolyzable to a monosaccharide, with an alcohol such as a fatty alcohol in an acid medium. For example, U.S. Pat. Nos. 5,527,892 and 5,770,543 describe alkyl glycosides and/or methods for their preparation. Suitable examples are commercially available under the names of Glucopon™ 220, 225, 425, 600 and 625, PLANTACARE®, and PLANTAPON®, all of which are available from Cognis Corporation of Ambler, Pa.

In another aspect, nonionic surfactants include, but are not limited to, alkoxylated methyl glucosides such as, for example, methyl gluceth-10, methyl gluceth-20, PPG-10 methyl glucose ether, and PPG-20 methyl glucose ether, available from Lubrizol Advanced Materials, Inc., under the trade names, Glucam® E10, Glucam® E20, Glucam® P10, and Glucam® P20, respectively; and hydrophobically modified alkoxylated methyl glucosides, such as PEG 120 methyl glucose dioleate, PEG-120 methyl glucose trioleate, and PEG-20 methyl glucose sesquistearate, available from Lubrizol Advanced Materials, Inc., under the trade names, Glucamate® DOE-120, Glucamate™ LT, and Glucamate™ SSE-20, respectively, are also suitable. Other exemplary hydrophobically modified alkoxylated methyl glucosides are disclosed in U.S. Pat. Nos. 6,573,375 and 6,727,357, the disclosures of which are hereby incorporated by reference in their entirety.

Other useful nonionic surfactants include water soluble silicones such as PEG-10 Dimethicone, PEG-12 Dimethicone, PEG-14 Dimethicone, PEG-17 Dimethicone, PPG-12 Dimethicone, PPG-17 Dimethicone and derivatized/functionalized forms thereof such as Bis-PEG/PPG-20/20 Dimethicone Bis-PEG/PPG-16/16 PEG/PPG-16/16 Dimethicone, PEG/PPG-14/4 Dimethicone, PEG/PPG-20/20 Dimethicone, PEG/PPG-20/23 Dimethicone, and Perfluorononylethyl Carboxydecyl PEG-10 Dimethicone.

The amount of the at least one surfactant (active weight basis) utilized in formulating the yield stress fluid of the invention ranges from about 1 to about 30 wt. % based on the weight of the total yield stress composition. In another aspect, the amount of the at least one surfactant utilized in the formulation ranges from about 3 to about 25 wt. %. In still another aspect, the amount of the at least one surfactant employed in the yield stress fluid ranges from about 5 to about 22 wt. %. In a further aspect, the amount of the at least one surfactant utilized ranges from about 6 to about 20 wt. %. In still a further aspect, the amount of at least one surfactant is about 10, 12, 14, 16, and 18 wt. % based on the total weight yield of the stress fluid.

In one embodiment of the invention, the weight ratio (based on active material) of anionic surfactant (non-ethoxylated and/or ethoxylated surfactant) to amphoteric surfactant can range from about 10:1 to about 2:1 in one aspect, and can be 9:1, 8:1, 7:1 6:1, 5:1, 4.5:1, 4:1, or 3:1 in another aspect. When employing an ethoxylated anionic surfactant and a non-ethoxylated anionic surfactant in combination with an amphoteric surfactant, the weight ratio (based on active material) of ethoxylated anionic surfactant to non-ethoxylated anionic surfactant to amphoteric surfactant can range from about 3.5:3.5:1 in one aspect to about 1:1:1 in another aspect.

In one embodiment, the yield stress value of the fluid is at least about 0.1 Pa in one aspect, at least about 0.5 Pa in another aspect, at least about 1 Pa in still another aspect, and at least about 1.5 Pa in a further aspect. In another embodiment, the yield stress of the fluid ranges from about 0.1 to about 20 Pa in one aspect, from about 0.5 Pa to about 10 Pa in another aspect, from about 1 to about 3 Pa in a further aspect, and from about 1.5 to about 3.5 in a still further aspect.

Optionally, the yield stress fluids of the invention can contain an electrolyte. Suitable electrolytes are known compounds and include salts of multivalent anions, such as potassium pyrophosphate, potassium tripolyphosphate, and sodium or potassium citrate, salts of multivalent cations, including alkaline earth metal salts such as calcium chloride and calcium bromide, as well as zinc halides, barium chloride and calcium nitrate, salts of monovalent cations with monovalent anions, including alkali metal or ammonium halides, such as potassium chloride, sodium chloride, potassium iodide, sodium bromide, and ammonium bromide, alkali metal or ammonium nitrates, and blends thereof. The amount of the electrolyte used will generally depend on the amount of the amphiphilic polymer incorporated, but may be used at concentration levels of from about 0.1 to about 4 wt. % in one aspect and from about 0.2 to about 2 wt. % in another aspect, based on the weight of the total composition.

The yield stress fluid must be easily pourable with a shear thinning index of less than 0.5 at shear rates between 0.1 and 1 reciprocal second, and an optical transmission of at least 10%. The yield stress fluid of the invention can be utilized in combination with a rheology modifier (thickener) to enhance the yield value of a thickened liquid. In one aspect, the yield stress fluid of the invention can be combined with a nonionic rheology modifier which rheology modifier when utilized alone does not have a sufficient yield stress value. Any rheology modifier is suitable, so long as such is soluble in water, stable and contains no ionic or ionizable groups. Suitable rheology modifiers include, but are not limited to natural gums (e.g., polygalactomannan gums selected from fenugreek, cassia, locust bean, tara and guar), modified cellulose (e.g., ethylhexylethylcellulose (EHEC), hydroxybutylmethylcellulose (HBMC), hydroxyethylmethylcellulose (NEMC), hydroxypropylmethylcellulose (HPMC), methyl cellulose (MC), hydroxyethylcellulose (HEC), hydroxypropylcellulose (HPC) and cetyl hydroxyethylcellulose) methylcellulose, polyethylene glycols (e.g., PEG 4000, PEG 6000, PEG 8000, PEG 10000, PEG 20000), polyvinyl alcohol, polyacrylamides (homopolymers and copolymers), and hydrophobically modified ethoxylated urethanes (HEUR); and mixtures thereof. The rheology modifier can be utilized in an amount ranging from about 0.5 to about 25 wt. % in one aspect, from about 1 to about 15 wt. % in another aspect, and from about 2 to about 10 wt. % in a further aspect, based on the weight of the total weight of the composition.

The yield stress fluids of the invention can be used in any application requiring yield stress properties. The yield stress fluids can be used alone or in combination with other fluids to enhance the yield stress values thereof.

In one embodiment, the yield stress fluids of the invention can be utilized to suspend particulate materials and insoluble droplets within an aqueous composition. Such fluids are useful in the oil and gas, personal care, and homecare industries.

In the oil and gas industry, the yield stress fluids of the invention can be used to enhance the yield stress value of drilling and hydraulic fracturing fluids, and can be employed to suspend borehole cuttings and fracturing proppants such as, for example, sand, sintered bauxite, glass balls, ceramic materials, polystyrene beads, and the like.

In the personal care industry, the yield stress fluids of the invention can be utilized to improve the yield stress properties of detersive compositions, hair and skin care compositions, as well as cosmetics, and can be utilized to suspend insoluble silicones, opacifiers and pearlescent agents (e.g., mica, coated mica), pigments, exfoliants, anti-dandruff agents, clay, swellable clay, laponite, gas bubbles, liposomes, microsponges, cosmetic beads, cosmetic microcapsules, and flakes. The yield stress fluids of the invention can stabilize these materials in suspension for at least one month at 23° C. in one aspect, at least 6 months in another aspect, and at least one year in a further aspect.

Exemplary bead components include, but are not limited to, agar beads, alginate beads, jojoba beads, gelatin beads, Styrofoam™ beads, polyacrylate, polymethylmethacrylate (PMMA), polyethylene beads, Unispheres™ and Unipearls™ cosmetic beads (Induchem USA, Inc., New York, N.Y.), Lipocapsule™, Liposphere™, and Lipopearl™ microcapsules (Lipo Technologies Inc., Vandalia, Ohio), and Confetti II™ dermal delivery flakes (United-Guardian, Inc., Hauppauge, N.Y.). Beads can be utilized as aesthetic materials or can be used to encapsulate benefit agents to protect them from the deteriorating effects of the environment or for optimal delivery, release and performance in the final product.

In one aspect, the cosmetic beads range in size from about 0.5 to about 1.5 mm. In another aspect, the difference in specific gravity of the bead and water is between about +/−0.01 and 0.5 g/ml in one aspect and from about +/−0.2 to 0.3 g/ml in another aspect.

In one aspect, the microcapsules range in size from about 0.5 to about 300 μm. In another aspect, the difference in specific gravity between the microcapsules and water is from about +/−0.01 to 0.5 g/ml. Non-limiting examples of microcapsule beads are disclosed in U.S. Pat. No. 7,786,027, the disclosure of which is herein incorporated by reference.

In one aspect of the invention, the amount of particulate component and/or insoluble droplets can range from about 0.1% to about 10% by weight based on the total weight of the composition.

While overlapping weight ranges for the various components and ingredients that can be contained in the yield stress fluids of the invention have been expressed for selected embodiments and aspects of the invention, it should be readily apparent that the specific amount of each component in the compositions will be selected from its disclosed range such that the amount of each component is adjusted such that the sum of all components in the composition will total 100 weight percent. The amounts employed will vary with the purpose and character of the desired product and can be readily determined by one skilled in the formulation art and from the literature.

This invention is illustrated by the following examples that are merely for the purpose of illustration and are not to be regarded as limiting the scope of the invention or the manner in which it can be practiced. Unless specifically indicated otherwise, parts and percentages are given by weight.

The following abbreviations and trade names are utilized in the examples.

| | |
|---|---|
| APE | Allyl Pentaerythritol |
| n-BA | n-Butyl Acrylate |
| BEM | Ethoxylated Behenyl Methacrylate, Sipomer BEM, Rhodia |
| Chembetaine ™ CAD | Cocamidopropyl Betaine (amphoteric surfactant), Lubrizol Advanced Materials, Inc. (35% active) |
| CYCLO | Cyclohexane |
| LMA | Lauryl Methacrylate |
| SMA | Stearyl Methacrylate |
| Sulfochem ™ ES-2 | Sodium Laureth Sulfate - 2 moles of ethoxylation (anionic surfactant), Lubrizol Advanced Materials, Inc. (26% active) |
| VA | Vinyl Acetate |
| VA-10 | Vinyl Decanoate |
| VP | N-Vinylpyrrolidone |

Examples 1 to 4

A free radical initiated dispersion polymerization is utilized to make crosslinked, nonionic, amphiphilic polymers of the invention. The polymerization reactor consists of a water-cooled resin kettle equipped with a reflux condenser, nitrogen purging tube, a mechanical agitator and a thermalcouple connected to a temperature control module. Admixtures of monomers, cross-linkers and processing aids are set forth in Table 1 are first added to the resin kettle, followed by polymerization solvent. The quantities of these components in grams for the various polymer preparations are shown in the table. While the reaction medium is heated to the target polymerization temperature, the reactor is purged with nitrogen for at least half an hour. As the reactor temperature reaches the set polymerization temperature, typically at about 67° C., the initiator solution is injected to start the polymerization. The polymerization is continued for at least 6 hours at 67° C. before a series of shots of additional initiator solution are injected into the reactor to reduce residual monomers to acceptable levels. The final product is recovered as a fine powder after the polymerization solvent is removed by rotary evaporator under vacuum followed by a gentle milling process. The total polymer solids in the final dispersion is typically at about 30 wt. %.

TABLE 1

| Example No. | NVP (wt. %)[1] | VA (wt. %)[1] | SMA (wt. %)[1] | LMA (wt. %)[1] | VA-10 (wt. %)[1] | APE (wt. %)[2] | Stabilizer[3] (wt. %)[2] | PGS[4] (wt. %)[2] | CYCLO (wt. %)[2] | Initiator[5] (wt. %)[2] |
|---|---|---|---|---|---|---|---|---|---|---|
| 1 | 84 | 15 | 1 | — | — | 0.1 | 6 | 1 | 231 | 0.12 |
| 2 | 84 | 15 | — | 1 | — | 0.1 | 6 | 1 | 231 | 0.12 |
| 3 | 64 | 35 | — | — | 1 | 0.1 | 6 | 1 | 230 | 0.12 |
| 4[6] | 84 | 15 | — | — | 1 | — | 6 | 1 | 231 | 0.12 |

[1]Based on the weight of the total monomers
[2]Based on the weight of the dry polymer
[3]50/30/20 (wt. %) copolymer of N-vinyl pyrrolidone/stearyl methacrylate/butyl methacrylate utilized as a dispersion polymerization stabilizer
[4]Reaction product $C_{20}$—$C_{24}$ substituted succinic anhydride and glycerin and or polyglycerol containing 2 to 6 glycerin units utilized as a process aid
[5]2,2'-azobis(2-methylbutyronitrile)
[6]Comparative Example Table 2 summarizes the constituent components of the various polymers prepared in Examples 1 to 4.

TABLE 2

| Example No. | Composition[1] monomer/(wt. %) | APE (wt. %)[2] |
|---|---|---|
| 1 | NVP(84)/VA(15)/SMA(1) | 0.1 |
| 2 | NVP(84)/VA(15)/LMA(1) | 0.1 |
| 3 | NVP(64)/VA(35)/VA-10(1) | 0.1 |
| 4[4] | NVP(84)/VA(15)/VA-10(1) | — |

[1]Weight % of polymerized monomer repeating unit
[2]Based on the weight of the dry polymer
[3]Calculated by the method in Example 1
[4]Comparative Example Example 5

This example illustrates the influence of crosslinked, nonionic, amphiphilic polymer prepared by dispersion polymerization on formulating yield stress fluids with an anionic surfactant in water. Samples containing 2 wt. % polymer (total polymer solids) and 2 wt. % SLS surfactant (active material) in water are prepared using the polymers prepared in Examples 1 to 4. The yield stress, viscosity and shear thinning index of these polymers are determined by oscillatory and steady shear measurements on a controlled stress rheometer (TA Instruments AR1000N rheometer, New Castle, Del.) with cone and plate geometry (40 mm cone with a cone angle of 2 degrees and 56 µm gap) at 25° C. The oscillatory measurements are performed at a fixed frequency ranging from 1 Hz to 0.001 Hz. The elastic and viscous moduli (G' and G" respectively) are obtained as a function of increasing stress amplitude. In cases where the swollen polymer particles create a jammed network, G' is larger than G" at low stress amplitudes but decreases at higher amplitudes crossing G" because of rupture of the network. The stress corresponding to the crossover of G' and G" is noted as the yield stress. A plot of viscosity versus shear rate is obtained from the steady shear measurements. The viscosity at a shear rate of 3 $s^{-1}$ is noted. The shear thinning index is obtained from a power law fit ($\eta=K\gamma^{n-1}$) in the shear rate range 0.1 to 1 $s^{-1}$ where $\eta$ is viscosity, $\gamma$ is shear rate, n is the shear thinning index and K is a constant. The optical clarity (expressed as percent transmittance or % T) of the samples is measured using a Brinkmann PC 910 colorimeter with a 420 nm filter. The yield stress, viscosity, shear thinning index, and optical clarity values are set forth in Table 3.

TABLE 3

| Polymer No. | Yield Stress (Pa) | Viscosity (Pa · s) | Shear Thinning Index | % T |
|---|---|---|---|---|
| 1 | 1.9 | 1.4 | 0.3 | 85 |
| 2 | 2.9 | 1.6 | 0.29 | 86 |
| 3 | 0.6 | 0.8 | 0.4 | 94 |
| 4 Comparative | None | 0.015 | 1.0 | 99 |

It is clear that the yield stress fluids formulated with the polymers of Examples 1 to 3 display high yield stresses, good shear thinning indices and excellent optical clarity. The comparative composition formulated with the polymer of Comparative Example 4 which does not contain any cross-linker has no yield stress value.

Examples 6 to 8

The following polymers are prepared by a dispersion polymerization process similar to Examples 1 to 4. Monomers, cross-linkers and processing aids used in the polymerization are given in Table 4

Table 5 summarizes the constituent components of the various polymers prepared in Examples 6 to 8.

TABLE 5

| Example No. | Composition Monomer (wt %) | APE (wt %)[2] |
|---|---|---|
| 6[1] | NVP(100) | 0.12 |
| 7 | NVP(82.5)/VA(14.5)/BEM(3) | 0.12 |
| 8 | NVP(82)/VA(14)/SMA(1)/BEM(3) | 0.12 |

[1]Comparative example
[2]Based on the weight of the dry polymer

Example 9

This example compares the performance of the hydrophilic homopolymer of Example 6 with that of a polymer of the invention based on Example 7. Samples containing 2 wt. % polymer solids and 7 wt. % surfactant (a mixture of 5 wt. % Sulfochem™ ALS-K and 2 wt. % Chembetaine™ CAD based on active material) in water are prepared and the yield stress measured as in Example 5. It is found that the control sample exhibits a yield stress of only 0.1 Pa whereas the invention samples show a yield stress of at least 3.3 Pa.

The ability of a polymer system to suspend active and/or aesthetically pleasing insoluble oily, gaseous and particulate materials is important from the standpoint of product efficacy and appeal. The long-term suspension of 1.2 mm sized beads with specific gravity of approximately 1.4 (Unisphere™ REL 552 from Induchem AG, Switzerland) is examined in Examples 16 to 22. A six dram vial (approximately 70 mm high×25 mm in diameter) is filled to the 50 mm point with each formulation. The beads are weighed into each of the above sample formulations (0.6 wt. % based on the weight of the total formulation) and stirred gently with a wooden spatula until they are uniformly dispersed throughout each sample. The vials are placed on a lab bench at ambient room temperature to age for a 16 week period. The bead suspension property of each sample is monitored on a daily basis. The suspension results are visually observed over the 16 week test period. It is observed that the beads remain in suspension (do not rise or settle) in the formulations of the invention for over 4 months at room temperature but suspension is not achieved in the control sample wherein the beads settle to the bottom of the vial in 2 weeks.

Example 10

This example illustrates a composition containing a polymer of the invention prepared by the dispersion polymer-

TABLE 4

| Ex. No. | NVP (wt. %) | VA (wt. %) | SMA (wt. %) | BEM[1] (wt. %) | APE (wt. %)[2] | Stabilizer[3] (wt. %)[2] | PGS[4] (wt. %)[2] | CYCLO (wt. %)[2] | EtAc (wt. %)[2] | Initiator[5] (wt. %)[2] |
|---|---|---|---|---|---|---|---|---|---|---|
| 6[6] | 100 | — | — | — | 0.12 | — | — | 631 | 270 | 0.1 |
| 7 | 82.5 | 14.5 | — | 3 | 0.12 | 6 | 1 | 157 | 67 | 0.1 |
| 8 | 82 | 14 | 1 | 3 | 0.12 | 6 | 1 | 159 | 68 | 0.1 |

[1]Ethoxylated (25) Behenyl Methacrylate (Sipomer BEM from Rhodia)
[2]Based on the weight of the dry polymer
[3]50/30/20 (wt. %) copolymer of N-vinyl pyrrolidone/stearyl methacrylate/butyl methacrylate utilized as a dispersion polymerization stabilizer
[4]Reaction product $C_{20}$—$C_{24}$ substituted succinic anhydride and glycerin and or polyglycerol containing 2 to 6 glycerin units utilized as a process aid
[5]2,2'-azobis(2-methylbutyronitrile)
[6]Comparative example ization process (Example 8) with a surfactant mixture containing greater than 75 wt. % of an anionic ethoxylated surfactant. A sample containing 2.5 wt. % polymer solids and 14 wt % surfactant (12 wt % anionic ethoxylated surfactant Sulfochem™ ES-2 and 2 wt % amphoteric surfactant Chembetaine™ CAD based on active material) is prepared and the yield stresses measured as in Example 5. The sample exhibited a yield stress of 2.1 Pa.

What is claimed is:

1. A yield stress fluid composition comprising water, at least one nonionic, crosslinked, amphiphilic polymer and at least one surfactant wherein the concentration of said polymer ranges from 0.5 to 5 wt. % and the concentration of said surfactant ranges from 1 to 30 wt. % (active weight basis), based on the total weight of the composition, wherein said at least one nonionic, crosslinked, amphiphilic polymer is devoid of ionic or ionizable moieties and is prepared from a monomer mixture comprising at least one hydrophilic monomer selected from a vinyl lactam; at least one hydrophobic monomer selected from one or more vinyl esters of aliphatic carboxylic acids containing 1 to 22 carbon atoms, one or more of esters of (meth)acrylic acid with alcohols containing 1 to 30 carbon atoms, and mixtures thereof, and an associative monomer and/or a semi-hydrophobic monomer, and wherein said yield stress is substantially independent of pH in the pH range from about 2 to about 14.

2. A composition of claim 1 wherein said polymer is prepared from a monomer mixture comprising at least 30 wt. % of said hydrophilic monomers and at least 5 wt. % of said hydrophobic monomers.

3. A composition of claim 2 wherein said monomer mixture comprises a crosslinking monomer which is present in an amount sufficient to be incorporated into said polymer from about 0.01 to about 1 wt. %, based on the total weight of the polymer.

4. A composition of claim 3 wherein the at least one crosslinking monomer is selected from polyallyl ethers of trimethylolpropane, polyallyl ethers of pentaerythritol, polyallyl ethers of sucrose, and mixtures thereof.

5. A composition of claim 1 wherein said vinyl lactam is N-vinyl pyrrolidone, and said one or more vinyl esters of aliphatic carboxylic acids containing 1 to 22 carbon atoms is selected from vinyl formate, vinyl acetate, vinyl propionate, vinyl butyrate, vinyl isobutyrate, vinyl valerate, vinyl hexanoate, vinyl 2-methylhexanate, vinyl 2-ethylhexanoate, vinyl iso-octanoate, vinyl nonanoate, vinyl neodecanoate, vinyl decanoate, vinyl versatate, vinyl laurate, vinyl palmitate, vinyl stearate, and mixtures thereof.

6. A composition of claim 1 wherein the at least one surfactant is selected from an anionic, cationic, amphoteric, nonionic, and mixtures thereof.

7. A composition of claim 6 wherein the at least one surfactant is selected from an anionic surfactant and an amphoteric surfactant.

8. A composition of claim 7 wherein the at least one anionic surfactant is ethoxylated.

9. A composition of claim 8 containing a mixture of surfactants wherein at least 75 wt. % of said surfactant mixture is composed of surfactants containing ethylene oxide moieties.

10. A composition of claim 7 wherein the at least one amphoteric surfactant is cocamidopropyl betaine.

11. A composition of claim 7 wherein the concentration of surfactant ranges from about 6 to about 20 wt. % (active material), based on the weight of the total composition.

12. A composition of claim 7 wherein the ratio of anionic surfactant to amphoteric surfactant (active material) is 10:1 to about 2:1.

13. A composition of claim 6 wherein the at least one anionic surfactant is selected from sodium dodecyl sulfate, sodium lauryl sulfate, sodium laureth sulfate, and mixtures thereof.

14. A composition of claim 1 wherein said yield stress is at least 0.1 Pa.

15. A composition of claim 1 wherein said polymer is a dispersion polymer.

16. A composition of claim 15 wherein said polymer is prepared from 95 to 99.5 wt. % of a combination of at least one vinyl lactam and at least one vinyl ester of a $C_1$-$C_{22}$ carboxylic acid, wherein at least 30 wt. % of said monomer combination is selected from a vinyl lactam, 0.05 to 5 wt. % of at least one $C_8$-$C_{22}$ alkyl (meth)acrylate, optionally up to 5 wt. % of an associative and/or a semi-hydrophobic monomer (said weight percent is based on the weight of the total monomers), and 0.01 to 1 wt. % of a crosslinking monomer (based on the weight of the dry polymer).

17. A composition of claim 16 wherein said vinyl lactam is N-vinyl pyrrolidone, and said vinyl ester is selected from vinyl formate, vinyl acetate, vinyl propionate, vinyl butyrate, vinyl isobutyrate, vinyl valerate, vinyl hexanoate, vinyl 2-methylhexanate, vinyl 2-ethylhexanoate, vinyl iso-octanoate, vinyl nonanoate, vinyl neodecanoate, vinyl decanoate, vinyl versatate, vinyl laurate, vinyl palmitate, vinyl stearate, and mixtures thereof, and said $C_8$-$C_{22}$ alkyl (meth)acrylate is selected from lauryl methacrylate, stearyl methacrylate, behenyl methacrylate, and mixtures thereof; and mixtures thereof.

18. A composition of claim 17 wherein said dispersion polymer is polymerized from a monomer mixture comprising 30 to 90 wt. % of N-vinyl pyrrolidone, 10 to 35 wt. % of at least one vinyl ester selected from vinyl acetate, vinyl propionate, vinyl butyrate, vinyl isobutyrate, vinyl valerate, vinyl hexanoate, vinyl 2-methylhexanate, vinyl 2-ethylhexanoate, vinyl iso-octanoate, vinyl nonanoate, vinyl neodecanoate, vinyl decanoate, vinyl versatate, vinyl laurate, vinyl palmitate, and vinyl stearate, 0 to 35 wt. % dimethylacrylamide, 0.5 to 5 wt. % of an $C_8$-$C_{22}$ alkyl (meth)acrylate selected from lauryl methacrylate, stearyl methacrylate, behenyl methacrylate, and mixtures thereof.

19. A composition of claim 18 wherein said dispersion polymer is prepared from a monomer mixture comprising N-vinyl pyrrolidone, vinyl acetate, and a $C_8$-$C_{22}$ alkyl (meth)acrylate selected from lauryl methacrylate, stearyl methacrylate, behenyl methacrylate, and mixtures thereof; and mixtures thereof.

20. A composition of claim 19 wherein said dispersion polymer is polymerized from a monomer mixture comprising 60 to 90 wt. % of N-vinyl pyrrolidone.

21. A composition in claim 16 further comprising an electrolyte.

22. A composition of claim 21 wherein said electrolyte is selected from potassium pyrophosphate, potassium tripolyphosphate, sodium or potassium citrate, calcium chloride and calcium bromide, zinc halides, barium chloride calcium nitrate, potassium chloride, sodium chloride, potassium iodide, sodium bromide, and ammonium bromide, alkali metal or ammonium nitrates, and blends thereof.

23. A composition of claim 16 further comprising an insoluble material, a particulate material, or combinations thereof.

24. A composition of claim 23 wherein said particulate material is selected from mica, coated mica, pigments, exfoliants, anti-dandruff agents, clay, swellable clay, laponite, microsponges, cosmetic beads, cosmetic microcapsules, flakes, and mixtures thereof.

25. A composition of claim 23 wherein said particulate material is selected from sand, sintered bauxite, glass balls, ceramic materials, polystyrene beads, and mixtures thereof.

26. A composition of claim 23 wherein said insoluble material is selected from gas bubbles, liposomes, silicones, and mixtures thereof.

27. A drilling fluid for use in drilling subterranean formations comprising a yield stress fluid of claim 16.

28. A hydraulic fracturing fluid for use in fracturing subterranean formations comprising a yield stress fluid of claim 16.

29. A hydraulic fracturing fluid of claim 28 further comprising a proppant.

30. A composition of claim 16 wherein said associative monomer is selected from cetyl polyethoxylated methacrylate, cetearyl polyethoxylated methacrylate, stearyl polyethoxylated (meth)acrylate, arachidyl polyethoxylated (meth)acrylate, behenyl polyethoxylated methacrylate, cerotyl polyethoxylated (meth)acrylate, montanyl polyethoxylated (meth)acrylate, melissyl polyethoxylated (meth)acrylate, and mixtures thereof; and mixtures thereof.

31. A composition of claim 15 wherein said dispersion polymer is prepared in the presence of a stabilizing polymer.

32. A composition of claim 31 wherein said stabilizing polymer is selected from a copolymer of N-vinyl pyrrolidone/stearyl methacrylate/butyl acrylate, the ester of the reaction product of a $C_{20}$ to $C_{24}$ alkyl substituted succinic anhydride and a polyol selected from glycerin and/or a polyglycerol containing 2 to 6 glycerin units, and mixtures thereof.

33. A composition of claim 1 wherein said associative monomer comprises (i) an ethylenically unsaturated end group portion; (ii) a polyoxyalkylene mid-section portion, and (iii) a hydrophobic end group portion containing 8 to 30 carbon atoms.

34. A composition of claim 33 wherein said associative monomer is represented by formulas VII and VIIA:

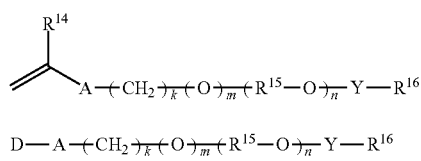

wherein $R^{14}$ is hydrogen or methyl; A is —$CH_2C(O)O$—, —$C(O)O$—, —$O$—, —$CH_2O$—, —$NHC(O)NH$—, —$C(O)NH$—, —Ar—$(CE_2)_z$-$NHC(O)O$—, —Ar—$(CE_2)_z$-$NHC(O)NH$—, or —$CH_2CH_2NHC(O)$—; Ar is a divalent arylene; E is H or methyl; z is 0 or 1; k is an integer ranging from about 0 to about 30, and m is 0 or 1, with the proviso that when k is 0, m is 0, and when k is in the range of 1 to about 30, m is 1; D represents a vinyl or an allyl moiety; $(R^{15}$—$O)_n$ is a polyoxyalkylene moiety, which can be a homopolymer, a random copolymer, or a block copolymer of $C_2$-$C_4$ oxyalkylene units, $R^{15}$ is a divalent alkylene moiety selected from $C_2H_4$, $C_3H_6$, or $C_4H_8$, and combinations thereof; and n is an integer in the range of about 2 to about 150; Y is —$R^{15}O$—, —$R^{15}NH$—, —$C(O)$—, —$C(O)NH$—, —$R^{15}NHC(O)NH$—, or —$C(O)NHC(O)$—; $R^{16}$ is a substituted or unsubstituted alkyl selected from a $C_8$-$C_{30}$ linear alkyl, a $C_8$-$C_{30}$ branched alkyl, a $C_8$-$C_{30}$ carbocyclic alkyl, a $C_2$-$C_{30}$ alkyl-substituted phenyl, an araalkyl substituted phenyl, and an aryl-substituted $C_2$-$C_{30}$ alkyl;

wherein the $R^{16}$ alkyl group, aryl group, phenyl group optionally comprises one or more substituents selected from the group consisting of a hydroxyl group, an alkoxyl group, benzyl group styryl group, and a halogen group.

35. A composition of claim 34 wherein said associative monomer is selected from lauryl polyethoxylated (meth)acrylate, cetyl polyethoxylated (meth)acrylate, cetearyl polyethoxylated (meth)acrylate, stearyl polyethoxylated (meth)acrylate, arachidyl polyethoxylated (meth)acrylate, behenyl polyethoxylated (meth)acrylate, cerotyl polyethoxylated (meth)acrylate, montanyl polyethoxylated (meth)acrylate, melissyl polyethoxylated (meth)acrylate, where the polyethoxylated portion of the monomer contains about 2 to about 50 ethylene oxide units, and said semi-hydrophobic monomer is selected from methoxy polyethyleneglycol (meth)acrylate or polyethyleneglycol (meth)acrylate, where the polyethoxylated portion of the monomer contains about 2 to about 50 ethylene oxide units.

36. A composition of claim 1 wherein said semi-hydrophobic monomer comprises (i) an ethylenically unsaturated end group portion; (ii) a polyoxyalkylene mid-section portion, and (iii) an end group portion selected from hydrogen or a group containing 1 to 4 carbon atoms.

37. A composition of claim 36 wherein said semi-hydrophobic monomer is selected from at least one monomer represented by formulas VIII and IX:

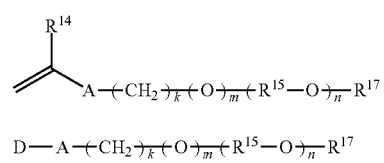

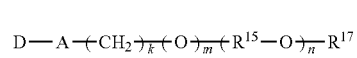

wherein $R^{14}$ is hydrogen or methyl; A is —$CH_2C(O)O$—, —$C(O)O$—, —$O$—, —$CH_2O$—, —$NHC(O)NH$—, —$C(O)NH$—, —Ar—$(CE_2)_z$-$NHC(O)O$—, —Ar—$(CE_2)_z$-$NHC(O)NH$—, or —$CH_2CH_2NHC(O)$—; Ar is a divalent arylene; E is H or methyl; z is 0 or 1; k is an integer ranging from about 0 to about 30, and m is 0 or 1, with the proviso that when k is 0, m is 0, and when k is in the range of 1 to about 30, m is 1; $(R^{15}$—$O)_n$ is a polyoxyalkylene moiety, which can be a homopolymer, a random copolymer, or a block copolymer of $C_2$-$C_4$ oxyalkylene units, $R^{15}$ is a divalent alkylene moiety selected from $C_2H_4$, $C_3H_6$, or $C_4H_8$, and combinations thereof; and n is an integer in the range of about 2 to about 150; $R^{17}$ is selected from hydrogen and a linear or branched $C_1$-$C_4$ alkyl group;

and D represents a vinyl or an allyl moiety.

38. A composition of claim 1 wherein said one or more of esters of (meth)acrylic acid with alcohols containing 1 to 30 carbon atoms is selected from methyl (meth)acrylate, ethyl (meth)acrylate, butyl (meth)acrylate, sec-butyl (meth)acrylate, iso-butyl (meth)acrylate, hexyl (meth)acrylate, heptyl (meth)acrylate, octyl (meth)acrylate, 2-ethylhexyl (meth) acrylate, decyl (meth)acrylate, isodecyl (meth)acrylate, lauryl (meth)acrylate, tetradecyl (meth)acrylate, hexadecyl (meth)acrylate, stearyl (meth)acrylate, behenyl (meth)acrylate, and mixtures thereof.

39. A composition of claim 1 wherein said at least one hydrophilic monomer further comprises a hydroxy($C_1$-$C_5$) alkyl (meth)acrylate.

40. A composition of claim 1 further comprising an insoluble material, a particulate material, or combinations thereof.

* * * * *